(12) United States Patent
Weinstein et al.

(10) Patent No.: US 6,391,025 B1
(45) Date of Patent: *May 21, 2002

(54) ELECTROSURGICAL SCALPEL AND METHODS FOR TISSUE CUTTING

(75) Inventors: Allan Weinstein, Los Altos, CA (US); Andrew R. Eggers, Ostrander, OH (US); Hira V. Thapliyal, Los Altos, CA (US); Philip E. Eggers, Dublin, OH (US)

(73) Assignee: ArthroCare Corporation, Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/041,934

(22) Filed: Mar. 13, 1998

Related U.S. Application Data

(63) Continuation-in-part of application No. 08/990,374, filed on Dec. 15, 1997, now Pat. No. 6,109,268, which is a continuation-in-part of application No. 08/485,219, filed on Jun. 7, 1995, now Pat. No. 5,697,281, which is a continuation-in-part of application No. 08/446,767, filed as application No. PCT/US94/05168 on May 10, 1994, now Pat. No. 5,697,909, which is a continuation-in-part of application No. 08/059,681, filed on May 10, 1993, now abandoned.

(51) Int. Cl.[7] .............................................. A61B 18/14
(52) U.S. Cl. ............................. 606/41; 606/45; 606/48; 604/114
(58) Field of Search .............................. 606/41, 45, 48, 606/49, 50, 32; 604/114; 607/99, 105, 113

(56) References Cited

U.S. PATENT DOCUMENTS

| | | |
|---|---|---|
| 2,050,904 A | 8/1936 | Trice |
| 4,033,351 A | 7/1977 | Hetzel .................... 128/303 |

(List continued on next page.)

FOREIGN PATENT DOCUMENTS

| | | | |
|---|---|---|---|
| EP | 0 703 461 A2 | 3/1996 | ........... G01R/27/02 |
| EP | 0 740 926 A2 | 11/1996 | ........... A61B/17/39 |

(List continued on next page.)

OTHER PUBLICATIONS

Slager et al. *JACC* 5(6) :1382–6 (1985).
V.E. Elsasser et al. *Acta Medicotechnica* vol. 24, No. 4, pp. 129–134 (1976).
E.V. Kramolowsky et al. *J. of Urology* vol. 143, pp. 275–277 (1990).

(List continued on next page.)

*Primary Examiner*—Lee Cohen
(74) *Attorney, Agent, or Firm*—John T. Raffle

(57) ABSTRACT

The present invention provides systems, apparatus and methods for selectively applying electrical energy to cut or incise structures in a patient's body. The electrosurgical systems and methods are particularly useful for removing tissue or ligaments from a patient's joint, such as the patellar ligament in the knee, in dermatological procedures, i.e., surface treatment of the patient's outer skin, such as the removal of pigmentations, vascular lesions (e.g., leg veins), scars, tattoos, etc., and in procedures for removing tissue in regions of the head and neck. The method of the present invention comprises positioning an electrosurgical probe adjacent the target tissue so that one or more electrode terminal(s) are brought into at least partial contact or close proximity with the target site in the presence of electrically conductive fluid. High frequency voltage is then applied between the electrode terminal(s) and one or more return electrode(s) and the electrode terminal(s) are translated, reciprocated or otherwise manipulated to cut through a portion of the tissue. The present invention volumetrically removes the tissue along the cutting pathway in a cool ablation process that minimizes thermal damage to surrounding tissue.

38 Claims, 17 Drawing Sheets

U.S. PATENT DOCUMENTS

| | | | |
|---|---|---|---|
| 4,040,426 A | 8/1977 | Morrison, Jr. | 128/303 |
| 4,043,342 A | 8/1977 | Morrison, Jr. | 128/303 |
| 4,116,198 A | 9/1978 | Roos | 128/303 |
| 4,184,492 A | 1/1980 | Meinke et al. | 128/303 |
| 4,202,337 A | 5/1980 | Hren et al. | 128/303 |
| 4,228,800 A | 10/1980 | Degler, Jr. et al. | 128/303 |
| 4,232,676 A | 11/1980 | Herczog | 128/303 |
| 4,248,231 A | 2/1981 | Herczog et al. | 128/303 |
| 4,326,529 A | 4/1982 | Doss | 128/303.1 |
| 4,381,007 A | 4/1983 | Doss | 228/303.1 |
| 4,476,862 A | 10/1984 | Pao | 128/303.17 |
| 4,532,924 A | 8/1985 | Auth et al. | 128/303.17 |
| 4,548,207 A | 10/1985 | Reimels | 128/303 |
| 4,567,890 A | 2/1986 | Ohta et al. | 128/303.13 |
| 4,593,691 A | 6/1986 | Lindstrom et al. | 128/303.14 |
| 4,674,499 A | 6/1987 | Pao | 128/303 |
| 4,682,596 A | 7/1987 | Bales et al. | 128/303 |
| 4,706,667 A | 11/1987 | Roos | 128/303 |
| 4,709,698 A | 12/1987 | Johnston et al. | 128/303 |
| 4,727,874 A | 3/1988 | Bowers et al. | 128/303 |
| 4,765,331 A | 8/1988 | Petruzzi et al. | 128/303 |
| 4,823,791 A | 4/1989 | D'Amelio et al. | 123/303 |
| 4,860,752 A | 8/1989 | Turner | 128/422 |
| 4,931,047 A | 6/1990 | Broadwin et al. | 604/22 |
| 4,936,301 A | 6/1990 | Rexroth et al. | 606/45 |
| 4,943,290 A | 7/1990 | Rexroth et al. | 606/45 |
| 4,955,377 A | 9/1990 | Lennox et al. | 128/401 |
| 4,967,765 A | 11/1990 | Turner et al. | 128/24 |
| 4,976,711 A | 12/1990 | Parins et al. | 606/48 |
| 4,979,948 A | 12/1990 | Geddes et al. | 606/33 |
| 4,998,933 A | 3/1991 | Eggers et al. | 606/41 |
| 5,007,908 A | 4/1991 | Rydell | 606/47 |
| 5,009,656 A | 4/1991 | Reimels | 606/48 |
| 5,035,696 A | 7/1991 | Rydell | 606/47 |
| 5,057,105 A | 10/1991 | Malone et al. | 606/28 |
| 5,057,106 A | 10/1991 | Kasevich et al. | 606/33 |
| 5,078,717 A | 1/1992 | Parins et al. | 606/48 |
| 5,080,660 A | 1/1992 | Buelna | 606/45 |
| 5,083,565 A | 1/1992 | Parins | 128/642 |
| 5,098,431 A | 3/1992 | Rydell | 606/48 |
| 5,108,391 A | 4/1992 | Flachenecker et al. | 606/38 |
| 5,112,330 A | 5/1992 | Nishigaki et al. | 606/46 |
| 5,122,138 A | 6/1992 | Manwaring | 606/46 |
| 5,125,928 A | 6/1992 | Parins et al. | 606/48 |
| 5,178,620 A | 1/1993 | Eggers et al. | 606/41 |
| 5,190,517 A | 3/1993 | Zieve et al. | 604/22 |
| 5,192,280 A | 3/1993 | Parins | 606/48 |
| 5,195,959 A | 3/1993 | Smith | 604/34 |
| 5,197,963 A | 3/1993 | Parins | 606/46 |
| 5,217,457 A | 6/1993 | Delahuerga et al. | 606/42 |
| 5,249,585 A | 10/1993 | Turner et al. | 607/99 |
| 5,267,994 A | 12/1993 | Gentelia et al. | 606/15 |
| 5,267,997 A | 12/1993 | Farin et al. | 606/38 |
| 5,273,524 A | 12/1993 | Fox et al. | 604/21 |
| 5,277,201 A | 1/1994 | Stern | 607/98 |
| 5,281,216 A | 1/1994 | Klicek | 606/42 |
| 5,281,218 A | 1/1994 | Imran | 606/41 |
| 5,290,282 A | 3/1994 | Casscells | 606/29 |
| 5,300,069 A | 4/1994 | Hunsberger et al. | 606/37 |
| 5,312,400 A | 5/1994 | Bales et al. | 606/41 |
| 5,314,406 A | 5/1994 | Arias et al. | 604/21 |
| 5,318,563 A | 6/1994 | Malis et al. | 606/38 |
| 5,324,254 A | 6/1994 | Phillips | 604/21 |
| 5,330,470 A | 7/1994 | Hagen | 606/42 |
| 5,334,140 A | 8/1994 | Phillips | 604/35 |
| 5,334,183 A | 8/1994 | Wuchinich | 606/46 |
| 5,336,220 A | 8/1994 | Ryan et al. | 604/22 |
| 5,342,357 A | 8/1994 | Nardella | 606/40 |
| 5,366,443 A | 11/1994 | Eggers et al. | 606/114 |
| 5,370,675 A | 12/1994 | Edwards et al. | 607/101 |
| 5,380,277 A | 1/1995 | Phillips | 604/33 |
| 5,383,876 A | 1/1995 | Nardella | 606/49 |
| 5,383,917 A | 1/1995 | Desai et al. | 607/702 |
| 5,395,312 A | 3/1995 | Desai | 604/22 |
| 5,417,687 A | 5/1995 | Nardella et al. | 606/32 |
| 5,419,767 A | 5/1995 | Eggers et al. | 604/114 |
| 5,441,499 A | 8/1995 | Fritzsch | 606/45 |
| 5,454,809 A | 10/1995 | Janssen | 606/41 |
| 5,496,312 A | 3/1996 | Klicek | 606/34 |
| 5,514,130 A | 5/1996 | Baker | 606/41 |
| 5,556,397 A | 9/1996 | Long et al. | 606/48 |
| 5,569,242 A | 10/1996 | Lax et al. | 606/42 |
| 5,584,872 A | 12/1996 | LaFontaine et al. | 607/116 |
| 5,609,151 A | 3/1997 | Mulier et al. | 128/642 |
| 5,647,869 A | 7/1997 | Goble et al. | 606/37 |
| 5,676,693 A | 10/1997 | LaFontaine | 607/116 |
| 5,681,282 A | 10/1997 | Eggers et al. | 604/114 |
| 5,683,366 A | 11/1997 | Eggers et al. | 604/114 |
| 5,697,281 A | 12/1997 | Eggers et al. | 604/114 |
| 5,697,536 A | 12/1997 | Eggers et al. | 604/114 |
| 5,697,882 A | 12/1997 | Eggers et al. | 604/114 |
| 5,697,909 A | 12/1997 | Eggers et al. | 604/114 |
| 5,700,262 A | 12/1997 | Acosta et al. | 606/48 |
| 5,725,524 A | 3/1998 | Mulier et al. | 606/41 |
| 5,749,869 A | 5/1998 | Lindenmeier et al. | 606/34 |
| 5,766,153 A | 6/1998 | Eggers et al. | 604/114 |
| 5,769,847 A | 6/1998 | Panescu et al. | 606/42 |
| 5,807,395 A | 9/1998 | Mulier et al. | 606/41 |
| 5,810,764 A | 9/1998 | Eggers et al. | 604/23 |
| 5,810,802 A | 9/1998 | Panescu et al. | 606/31 |
| 5,843,078 A | * 12/1998 | Sharkey | 606/41 |
| 5,885,277 A | 3/1999 | Korth | 606/35 |
| 5,891,095 A | 4/1999 | Eggers et al. | 604/114 |
| 5,897,553 A | * 4/1999 | Mulier et al. | 606/45 |
| 5,944,715 A | 8/1999 | Goble et al. | 606/41 |
| 6,004,319 A | 12/1999 | Goble et al. | 606/48 |
| 6,013,076 A | 1/2000 | Goble et al. | 606/41 |
| 6,015,406 A | 1/2000 | Goble et al. | 606/41 |
| 6,027,501 A | 2/2000 | Goble et al. | 606/41 |

FOREIGN PATENT DOCUMENTS

| | | | | |
|---|---|---|---|---|
| EP | | 0 754 437 | 1/1997 | A61B/17/39 |
| GB | | 2 308 979 | 7/1997 | |
| GB | | 2 308 980 | 7/1997 | |
| GB | | 2 308 981 | 7/1997 | |
| GB | | 2327350 | 1/1999 | A61B/17/39 |
| GB | | 2327351 | 1/1999 | A61B/17/39 |
| GB | | 2327352 | 1/1999 | A61B/17/39 |
| JP | | 57-57802 | 4/1982 | A61B/1/100 |
| JP | | 57-117843 | 7/1982 | A61B/17/39 |
| WO | WO | 90/07303 | 7/1990 | A61B/17/39 |
| WO | WO | 92/21278 | 12/1992 | A61B/5/04 |
| WO | WO | 93/13816 | 7/1993 | A61B/17/36 |
| WO | | 93/20747 | 10/1993 | A61B/5/00 |
| WO | | 94/04220 | 3/1994 | A61N/1/06 |
| WO | | 94/08654 | 4/1994 | A61M/37/00 |
| WO | | 95/34259 | 12/1995 | A61F/5/48 |
| WO | | 96/00042 | 1/1996 | A61B/17/39 |
| WO | | 97/00646 | 1/1997 | A61B/17/39 |
| WO | | 97/00647 | 1/1997 | A61B/17/39 |
| WO | | 97/24073 | 7/1997 | A61B/17/39 |
| WO | | 97/24993 | 7/1997 | A61B/17/39 |
| WO | | 97/24994 | 7/1997 | A61B/17/39 |
| WO | WO | 97/48345 | 12/1997 | A61B/17/39 |
| WO | | 97/48346 | 12/1997 | A61B/17/39 |
| WO | | 98/07468 | 2/1998 | |
| WO | | 98/27879 | 7/1998 | A61B/17/36 |
| WO | | 98/27880 | 7/1998 | A61B/17/39 |
| WO | WO | 98/34558 | 8/1998 | A61B/18/00 |
| WO | | 99/51158 | 10/1999 | A61B/17/39 |

OTHER PUBLICATIONS

J.W. Ramsey et al. *Urological Research* vol. 13, pp. 99–102 (1985).

R. Tucker et al., Abstract P14–11, p. 248, "A Bipolar Electrosurgical Turp Loop".

R. Tucker et al. *J. of Urology* vol. 141, pp. 662–665, (1989).

R. Tucker et al. *Urological Research* vol. 18, pp. 291–294 (1990).

M. Buchelt et al. *Lasers In Surgery and Medecine* 11:271–279 (1991).

J. Costello *Lasers in Surgery and Medecine* 12:121–124 (1992).

P.C. Nardella (1989) *SPIE* 1068:42–49 Radio Frequency Energy and Impedance Feedback.

Rand et al. (1985) *J. Arthro. Surg.* 1:242–246 Effect of Electrocautery on Fresh Human Articular Cartilage.

Pearce, John A. (1986) *Electrosurgery*, pp. 17, 69–75, 87, John Wiley & Sons, New York.

Tucker et al. (1989) Abstract P14–11, $7^{th}$ World Congress on Endourolgy and ESWL, Nov. 27–30, Kyoto, Japan.

Slager et al. *Z. Kardiol.* 76:Suppl. 6, 67–71 (1987).

\* cited by examiner

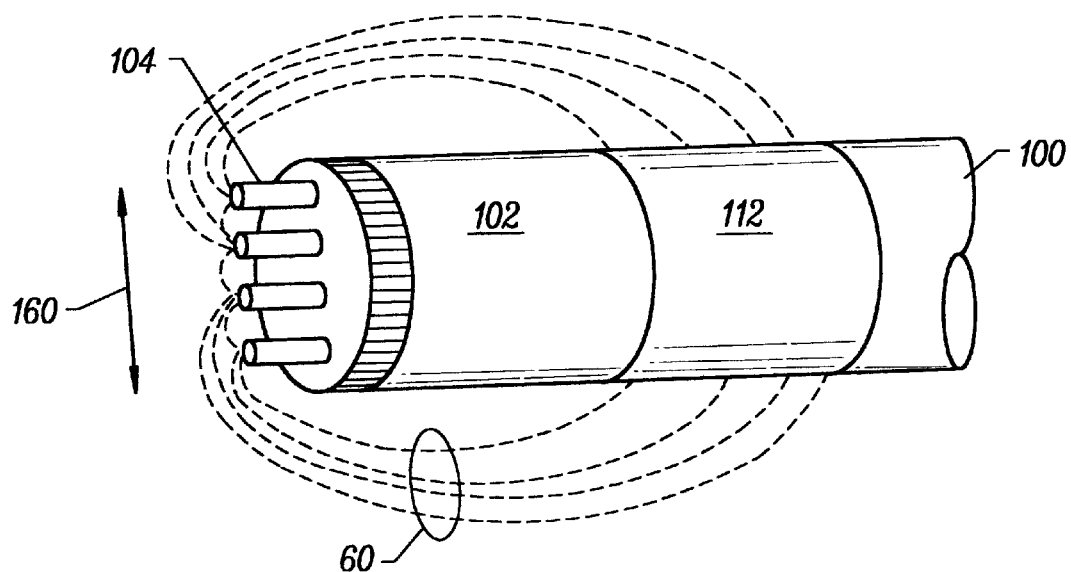
FIG. 10
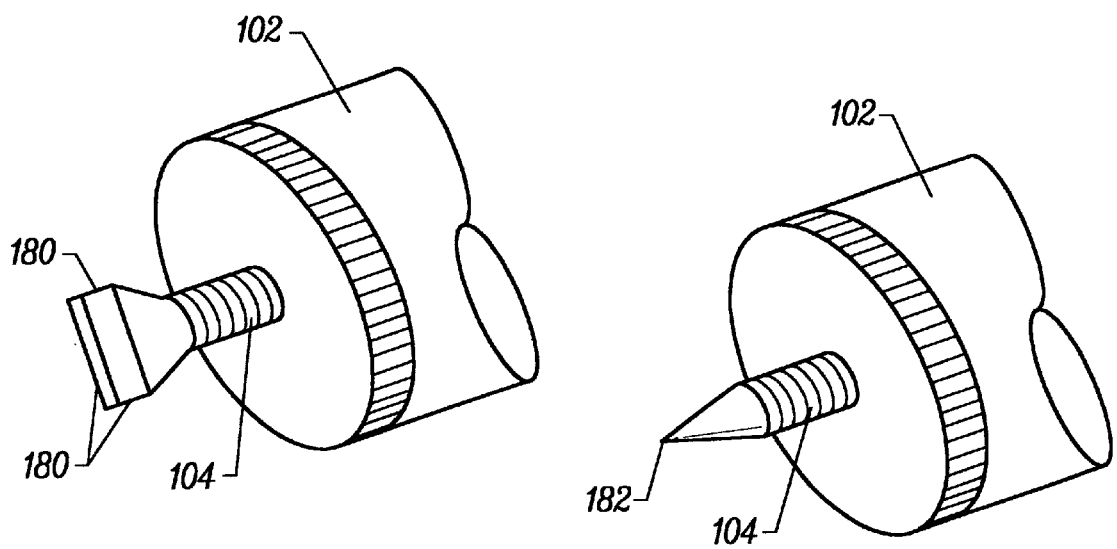
FIG. 11
FIG. 12

ELECTROSURGICAL SCALPEL AND METHODS FOR TISSUE CUTTING

RELATED APPLICATIONS

The present invention is a continuation-in-part of U.S. patent application Ser. No. 08/990,374 entitled "Electrosurgical Systems and Methods For Endoscopic Sinus Surgery" filed Dec. 15, 1997, now U.S. Pat. No. 6,109,268, which is a continuation-in-part of U.S. patent application Ser. No. 08/485,219 (now U.S. Pat. No. 5,697,281), filed on Jun. 7, 1995 which was a continuation-in-part of Ser. No. 08/446,767, which was the National Phase of PCT International Application, U.S. National Phase Ser. No. PCT/US94/05168 (now U.S. Pat. No. 5,697,909), filed on May 10, 1994, which was a continuation-in-part of application Ser. No. 08/059,681, filed on May 10, 1993 now abandoned, the complete disclosures of which are incorporated herein by reference for all purposes.

The present invention is related to commonly assigned co-pending Provisional Patent Application No. 60/062,996, filed Oct. 23, 1997, non-provisional U.S. patent application Ser. No. 08/977,845, filed Nov. 25, 1997, U.S. patent application Ser. No. 08/942,580, filed Oct. 2, 1997, U.S. application Ser. No. 08/753,227, filed Nov. 22, 1996, and U.S. application Ser. No. 08/687,792, filed Jul. 18, 1996, the complete disclosures of which are incorporated herein by reference for all purposes. The present invention is also related to commonly assigned U.S. Pat. No. 5,683,366, filed Nov. 22, 1995, the complete disclosure of which is incorporated herein by reference for all purposes.

BACKGROUND OF THE INVENTION

The present invention relates generally to the field of electrosurgery, and more particularly to surgical devices and methods which employ high frequency electrical energy to cut, ablate, resect, incise or otherwise remove body structures.

The field of electrosurgery includes a number of loosely related surgical techniques which have in common the application of electrical energy to modify the structure or integrity of patient tissue. Electrosurgical procedures usually operate through the application of very high frequency currents to cut or ablate tissue structures, where the operation can be monopolar or bipolar. Monopolar techniques rely on external grounding of the patient, where the surgical device defines only a single electrode pole. Bipolar devices comprise both electrodes for the application of current between their surfaces.

Electrosurgical procedures and techniques are particularly advantageous since they generally reduce patient bleeding and trauma associated with cutting operations. Current electrosurgical devices and procedures, however, suffer from a number of disadvantages. For example, conventional electrosurgical cutting devices typically operate by creating a voltage difference between the active electrode and the target tissue, causing an electrical arc to form across the physical gap between the electrode and tissue. At the point of contact of the electric arcs with tissue, rapid tissue heating occurs due to high current density between the electrode and tissue. This high current density causes cellular fluids to rapidly vaporize into steam, thereby producing a "cutting effect" along the pathway of localized tissue heating. Thus, the tissue is parted along the pathway of evaporated cellular fluid, inducing undesirable collateral tissue damage in regions surrounding the target tissue site.

Further, monopolar devices generally direct electric current along a defined path from the exposed or active electrode through the patient's body to the return electrode, which is externally attached to a suitable location on the patient. This creates the potential danger that the electric current will flow through undefined paths in the patient's body, thereby increasing the risk of unwanted electrical stimulation to portions of the patient's body. In addition, since the defined path through the patient's body has a relatively high impedance (because of the large distance or resistivity of the patient's body), large voltage differences must typically be applied between the return and active electrodes in order to generate a current suitable for ablation or cutting of the target tissue. This current, however, may inadvertently flow along body paths having less impedance than the defined electrical path, which will substantially increase the current flowing through these paths, possibly causing damage to or destroying surrounding tissue.

Bipolar electrosurgical devices have an inherent advantage over monopolar devices because the return current path does not flow through the patient. In bipolar electrosurgical devices, both the active and return electrode are typically exposed so that they may both contact tissue, thereby providing a return current path from the active to the return electrode through the tissue. One drawback with this configuration, however, is that the return electrode may cause tissue desiccation or destruction at its contact point with the patient's tissue. In addition, the active and return electrodes are typically positioned close together to ensure that the return current flows directly from the active to the return electrode. The close proximity of these electrodes generates the danger that the current will short across the electrodes, possibly impairing the electrical control system and/or damaging or destroying surrounding tissue.

The use of electrosurgical procedures (both monopolar and bipolar) in electrically conductive environments can be further problematic. For example, many arthroscopic procedures require flushing of the region to be treated with isotonic saline (also referred to as normal saline), both to maintain an isotonic environment and to keep the field of viewing clear. The presence of saline, which is a highly conductive electrolyte, can also cause shorting of the electrosurgical electrode in both monopolar and bipolar modes. Such shorting causes unnecessary heating in the treatment environment and can further cause non-specific tissue destruction.

SUMMARY OF THE INVENTION

The present invention provides systems, apparatus and methods for selectively applying electrical energy to cut or incise structures in a patient's body. The electrosurgical systems and methods are particularly useful for removing tissue or ligaments from a patient's joint, such as the patellar ligament in the knee, in dermatological procedures, i.e., surface treatment of the patient's outer skin, such as the removal of pigmentations, vascular lesions (e.g., leg veins), scars, tattoos, etc., and in procedures for removing tissue in regions of the head and neck, such as UPPP procedures, tonsillectomies, adenoidectomies and the like.

In one method of the present invention, an electrosurgical probe is positioned adjacent the target tissue so that one or more electrode terminal(s) are brought into at least partial contact or close proximity with the target site in the presence of electrically conductive fluid. High frequency voltage is then applied between the electrode terminal(s) and one or more return electrode(s) and the electrode terminal(s) are translated, reciprocated or otherwise manipulated to cut through a portion of the tissue. In some embodiments, the electrically conductive fluid, e.g., isotonic saline or conductive gel, is delivered or applied to the target site to substantially surround the electrode terminal(s) with the fluid. In other embodiments, the electrode terminal(s) are immersed within the electrically conductive fluid, such as in arthroscopic procedures. In both embodiments, the high frequency voltage is preferably selected to effect a controlled depth of hemostasis of severed blood vessels within the tissue, which greatly improves the surgeon's view of the surgical site.

In a specific configuration, the tissue is cut by molecular dissociation or disintegration processes. Conventional electrosurgery cuts through tissue by rapidly heating the tissue until cellular fluids explode, producing a cutting effect along the pathway of localized heating. The present invention volumetrically removes the tissue along the cutting pathway in a cool ablation process that minimizes thermal damage to surrounding tissue. In these embodiments, the high frequency voltage applied to the electrode terminal(s) is sufficient to vaporize an electrically conductive fluid (e.g., gel or saline) between the electrode terminal(s) and the tissue. Within the vaporized fluid, an ionized plasma is formed and charged particles (e.g., electrons) are accelerated towards the tissue to cause the molecular breakdown or disintegration of several cell layers of the tissue. This molecular dissociation is accompanied by the volumetric removal of the tissue along the pathway of tissue cutting. The short range of the accelerated charged particles within the plasma layer confines the molecular dissociation process to the cutting pathway to minimize damage and necrosis to the surrounding tissue. This process can be precisely controlled to effect the volumetric removal of tissue as thin as 10 to 150 microns with minimal heating of, or damage to, surrounding or underlying tissue structures. A more complete description of this phenomena is described in commonly assigned U.S. Pat. No. 5,683,366, the complete disclosure of which is incorporated herein by reference.

In an exemplary embodiment, a method for removing a ligament from a joint, e.g., the patellar ligament or a cruciate ligament from the knee, includes positioning the electrosurgical probe adjacent the ligament and applying high frequency electrical energy between one or more electrode terminal(s) and one or more return electrode(s) in the presence of electrically conductive fluid. The probe is then translated so that the electrode terminal(s) volumetrically remove ligament tissue along the cutting path. In an exemplary embodiment, two spaced electrode terminals on the distal end of the probe are positioned on either side of the ligament. The probe is advanced along the length of the ligament while high frequency electrical energy is applied between the electrode terminal(s) and a return electrode to remove or cut the tissue or other structures surrounding the ligament. The residual heat from the electrical energy also provides simultaneous hemostasis of severed blood vessels, which increases visualization and improves recovery time for the patient. In addition, the ability to simultaneously cut through tissue on either side of the ligament decreases the length of the procedure, which further improves patient recovery time. The ligament is then removed by severing the upper and lower portions and removing the central portion of the ligament from the joint either with a conventional scalpel or with one of the electrosurgical scalpels of the present invention.

Apparatus according to the present invention generally include an electrosurgical instrument, such as a probe or catheter, having a shaft with proximal and distal ends, one or more electrode terminal(s) at the distal end and one or more connectors coupling the electrode terminal(s) to a source of high frequency electrical energy. The electrode terminal(s) are preferably designed for cutting tissue; i.e., they typically have a distal edge or point. In the exemplary embodiment, the electrode terminal(s) are aligned with each other to form a linear cutting path through the tissue.

The apparatus preferably further includes a fluid delivery element for delivering electrically conducting fluid to the electrode terminal(s) and the target site. The fluid delivery element may be located on the probe, e.g., a fluid lumen or tube, or it may be part of a separate instrument. Alternatively, an electrically conducting gel or spray, such as a saline electrolyte or other conductive gel, may be applied the target site. In this embodiment, the apparatus may not have a fluid delivery element. In both embodiments, the electrically conducting fluid preferably generates a current flow path between the electrode terminal(s) and one or more return electrode(s). In an exemplary embodiment, the return electrode is located on the probe and spaced a sufficient distance from the electrode terminal(s) to substantially avoid or minimize current shorting therebetween and to shield the return electrode from tissue at the target site.

In a specific configuration, the electrosurgical probe includes an electrically insulating electrode support member having a tissue treatment surface at the distal end of the probe. One or more electrode terminal(s) are coupled to, or integral with, the electrode support member such that the electrode terminal(s) are spaced from the return electrode. In one embodiment, the probe includes a plurality of electrode terminal(s) having distal edges linearly aligned with each other to form a sharp cutting path for cutting tissue. The electrode terminals are preferably electrically isolated from each other, and they extend about 0.2 mm to about 10 mm distally from the tissue treatment surface of the electrode support member. In this embodiment, the probe may further include one or more lumens for delivering electrically conductive fluid to one or more openings around the tissue treatment surface of the electrode support member. In an exemplary embodiment, the lumen extends through a fluid tube exterior to the probe shaft that ends proximal to the return electrode.

In another aspect of the invention, the electrode support member comprises a plurality of wafer layers bonded together, e.g., by a glass adhesive or the like. The wafer layers each have conductive strips plated or printed thereon to form the electrode terminal(s) and the return electrode(s). In one embodiment, the proximal end of the wafer layers will have a number of holes extending from the conductor strips to an exposed surface of the wafer layers for connection to electrical conductor lead traces in the electrosurgical probe or handpiece. The wafer layers preferably comprise a ceramic material, such as alumina, and the electrode will preferably comprise a metallic material, such as gold, platinum, tungsten, palladium, silver or the like.

BRIEF DESCRIPTION OF THE DRAWINGS

FIG. 10 is a detailed end view of an electrosurgical probe having an elongate, linear array of electrode terminals suitable for use in surgical cutting;

FIG. 11 is a detailed view of a single electrode terminal having a flattened end at its distal tip;

FIG. 12 is a detailed view of a single electrode terminal having a pointed end at its distal tip;

DESCRIPTION OF SPECIFIC EMBODIMENTS

Figure 1:
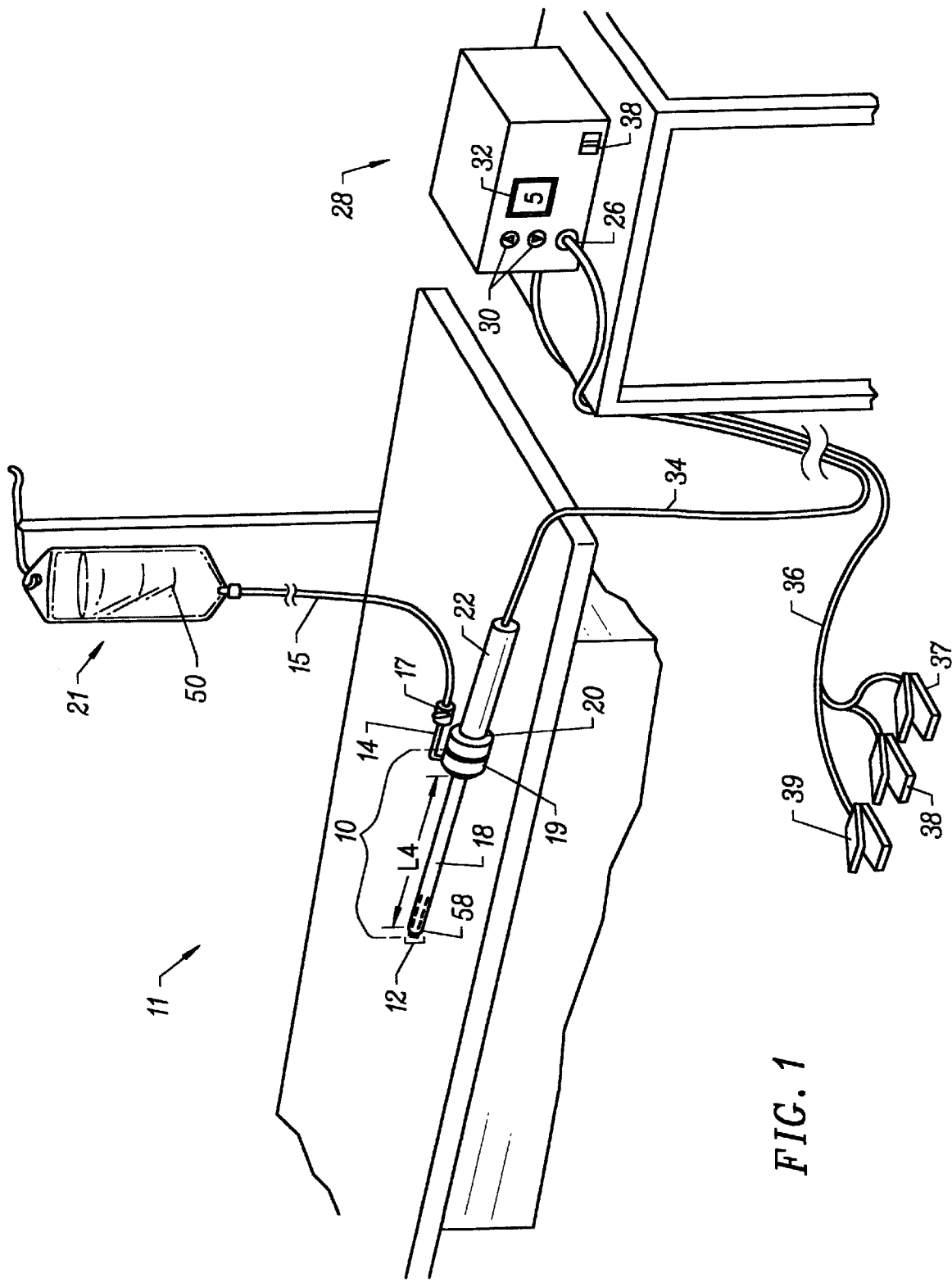
FIG. 1 is a perspective view of an electrosurgical system incorporating a power supply and an electrosurgical probe for tissue ablation, resection, incision, contraction and for vessel hemostasis according to the present invention.

The present invention is useful in procedures where the tissue site is flooded or submerged with an electrically conducting fluid, such as arthroscopic surgery of the knee, shoulder, ankle, hip, elbow, hand or foot. In addition, tissues which may be treated by the system and method of the present invention include, but are not limited to, prostate tissue and leiomyomas (fibroids) located within the uterus, gingival tissues and mucosal tissues located in the mouth, tumors, scar tissue, myocardial tissue, collagenous tissue within the eye or epidermal and dermal tissues on the surface of the skin. The present invention is also useful for resecting tissue within accessible sites of the body that are suitable for electrode loop resection, such as the resection of prostate tissue, leiomyomas (fibroids) located within the uterus and other diseased tissue within the body.

The present invention is also useful for procedures in the head and neck, such as the ear, mouth, pharynx, larynx, esophagus, nasal cavity and sinuses. These procedures may be performed through the mouth or nose using speculae or gags, or using endoscopic techniques, such as functional endoscopic sinus surgery (FESS). These procedures may include the removal of swollen tissue, chronically-diseased inflamed and hypertrophic mucus linings, polyps and/or neoplasms from the various anatomical sinuses of the skull, the turbinates and nasal passages, in the tonsil, adenoid, epi-glottic and supra-glottic regions, and salivary glands, submucus resection of the nasal septum, excision of diseased tissue and the like. In other procedures, the present invention may be useful for cutting, resection, ablation and/or hemostasis of tissue in procedures for treating snoring and obstructive sleep apnea (e.g., UPPP procedures), for gross tissue removal, such as tonsillectomies, adenoidectomies, tracheal stenosis and vocal cord polyps and lesions, or for the resection or ablation of facial tumors or tumors within the mouth and pharynx, such as glossectomies, laryngectomies, acoustic neuroma procedures and nasal ablation procedures. In addition, the present invention is useful for procedures within the ear, such as stapedotomies, tympanostomies or the like.

The present invention may also be useful for cosmetic and plastic surgery procedures in the head and neck. For example, the present invention is particularly useful for ablation and sculpting of cartilage tissue, such as the cartilage within the nose that is sculpted during rhinoplasty procedures. The present invention may also be employed for skin tissue removal and/or collagen shrinkage in the epidermis or dermis tissue in the head and neck, e.g., the removal of pigmentations, vascular lesions (e.g., leg veins), scars, tattoos, etc., and for other surgical procedures on the skin, such as tissue rejuvenation, cosmetic eye procedures (blepharoplasties), wrinkle removal, tightening muscles for facelifts or browlifts, hair removal and/or transplant procedures, etc.

For convenience, the remaining disclosure will be directed specifically to the removal of ligaments within a joint during an arthroscopic procedure and to surgical procedures on the skin, but it will be appreciated that the system and method can be applied equally well to procedures involving other tissues of the body, as well as to other procedures including open procedures, intravascular procedures, urology, laparascopy, arthroscopy, thoracoscopy or other cardiac procedures, cosmetic surgery, orthopedics, gynecology, otorhinolaryngology, spinal and neurologic procedures, oncology and the like.

In the present invention, high frequency (RF) electrical energy is applied to one or more electrode terminals in the presence of electrically conductive fluid to remove and/or modify the structure of tissue structures. Depending on the specific procedure, the present invention may be used to: (1) volumetrically remove tissue or cartilage (i.e., ablate or effect molecular dissociation of the tissue structure); (2) cut or resect tissue; and/or (3) coagulate severed blood vessels.

In one method of the present invention, the tissue structures are cut by volumetrically removing or ablating tissue along a cutting path. In this procedure, a high frequency voltage difference is applied between one or more electrode terminal(s) and one or more return electrode(s) to develop high electric field intensities in the vicinity of the target tissue site. The high electric field intensities lead to electric field induced molecular breakdown of target tissue through molecular dissociation (rather than thermal evaporation or carbonization). Applicant believes that the tissue structure is volumetrically removed through molecular disintegration of larger organic molecules into smaller molecules and/or atoms, such as hydrogen, oxides of carbon, hydrocarbons and nitrogen compounds. This molecular disintegration completely removes the tissue structure, as opposed to dehydrating the tissue material by the removal of liquid within the cells of the tissue, as is typically the case with electrosurgical desiccation and vaporization.

The high electric field intensities may be generated by applying a high frequency voltage that is sufficient to vaporize an electrically conducting fluid over at least a portion of the electrode terminal(s) in the region between the distal tip of the electrode terminal(s) and the target tissue. The electrically conductive fluid may be a gas or liquid, such as isotonic saline, delivered to the target site, or a viscous fluid, such as a gel, that is located at the target site. In the latter embodiment, the electrode terminal(s) are submersed in the electrically conductive gel during the surgical procedure. Since the vapor layer or vaporized region has a relatively high electrical impedance, it increases the voltage differential between the electrode terminal tip and the tissue and causes ionization within the vapor layer due to the presence of an ionizable species (e.g., sodium when isotonic saline is the electrically conducting fluid). This ionization, under optimal conditions, induces the discharge of energetic electrons and photons from the vapor layer and to the surface of the target tissue. This energy may be in the form of energetic photons (e.g., ultraviolet radiation), energetic particles (e.g., electrons) or a combination thereof. A more detailed description of this cold ablation phenomena, termed Coblation™, can be found in commonly assigned U.S. Pat. No. 5,683,366 the complete disclosure of which is incorporated herein by reference.

The present invention applies high frequency (RF) electrical energy in an electrically conducting fluid environment to remove (i.e., resect, cut or ablate) a tissue structure, and to seal transected vessels within the region of the target tissue. The present invention is particularly useful for sealing larger arterial vessels, e.g., on the order of 1 mm or greater. In some embodiments, a high frequency power supply is provided having an ablation mode, wherein a first voltage is applied to an electrode terminal sufficient to effect molecular dissociation or disintegration of the tissue, and a coagulation mode, wherein a second, lower voltage is applied to an electrode terminal (either the same or a different electrode) sufficient to achieve hemostasis of severed vessels within the tissue. In other embodiments, an electrosurgical probe is provided having one or more coagulation electrode(s) configured for sealing a severed vessel, such as an arterial vessel, and one or more electrode terminals configured for either contracting the collagen fibers within the tissue or removing (ablating) the tissue, e.g., by applying sufficient energy to the tissue to effect molecular dissociation. In the latter embodiments, the coagulation electrode(s) may be configured such that a single voltage can be applied to coagulate with the coagulation electrode(s), and to ablate or contract with the electrode terminal(s). In other embodiments, the power supply is combined with the coagulation probe such that the coagulation electrode is used when the power supply is in the coagulation mode (low voltage), and the electrode terminal(s) are used when the power supply is in the ablation mode (higher voltage).

In the method of the present invention, one or more electrode terminals are brought into close proximity to tissue at a target site, and the power supply is activated in the ablation mode such that sufficient voltage is applied between the electrode terminals and the return electrode to volumetrically remove the tissue through molecular dissociation, as described below. During this process, vessels within the tissue will be severed. Smaller vessels will be automatically sealed with the system and method of the present invention. Larger vessels, and those with a higher flow rate, such as arterial vessels, may not be automatically sealed in the ablation mode. In these cases, the severed vessels may be sealed by activating a control (e.g., a foot pedal) to reduce the voltage of the power supply into the coagulation mode. In this mode, the electrode terminals may be pressed against the severed vessel to provide sealing and/or coagulation of the vessel. Alternatively, a coagulation electrode located on the same or a different probe may be pressed against the severed vessel. Once the vessel is adequately sealed, the surgeon activates a control (e.g., another foot pedal) to increase the voltage of the power supply back into the ablation mode.

The electrosurgical probe will comprise a shaft or a handpiece having a proximal end and a distal end which supports one or more electrode terminal(s). The shaft or handpiece may assume a wide variety of configurations, with the primary purpose being to mechanically support the active electrode and permit the treating physician to manipulate the electrode from a proximal end of the shaft. The shaft may be rigid or flexible, with flexible shafts optionally being combined with a generally rigid external tube for mechanical support. Flexible shafts may be combined with pull wires, shape memory actuators, and other known mechanisms for effecting selective deflection of the distal end of the shaft to facilitate positioning of the electrode array. The shaft will usually include a plurality of wires or other conductive elements running axially therethrough to permit connection of the electrode array to a connector at the proximal end of the shaft. Specific shaft designs will be described in detail in connection with the figures hereinafter.

The current flow path between the electrode terminal(s) and the return electrode(s) may be generated by submerging the tissue site in an electrical conducting fluid (e.g., within a viscous fluid, such as an electrically conductive gel) or by directing an electrically conducting fluid along a fluid path to the target site (i.e., a liquid, such as isotonic saline, or a gas, such as argon). This latter method is particularly effective in a dry environment (i.e., the tissue is not submerged in fluid) because the electrically conducting fluid provides a suitable current flow path from the electrode terminal to the return electrode. A more complete description of an exemplary method of directing electrically conducting fluid between the active and return electrodes is described in parent application Ser. No. 08/485,219, filed Jun. 7, 1995, previously incorporated herein by reference.

In some procedures, it may also be necessary to retrieve or aspirate the electrically conductive fluid after it has been directed to the target site. For example, in procedures in the nose, mouth or throat, it may be desirable to aspirate the fluid so that it does not flow down the patient's throat. In addition, it may be desirable to aspirate small pieces of tissue that are not completely disintegrated by the high frequency energy, or other fluids at the target site, such as blood, mucus, the gaseous products of ablation, etc. Accordingly, the system of the present invention will usually include a suction lumen in the probe, or on another instrument, for aspirating fluids from the target site.

The present invention may use a single active electrode terminal or a plurality of electrodes distributed across a contact surface of a probe (e.g., in a linear fashion). In the latter embodiment, the electrode array usually includes a plurality of independently current-limited and/or power-controlled electrode terminals to apply electrical energy selectively to the target tissue while limiting the unwanted application of electrical energy to the surrounding tissue and environment resulting from power dissipation into surrounding electrically conductive liquids, such as blood, normal saline, electrically conductive gel and the like. The electrode terminals may be independently current-limited by isolating the terminals from each other and connecting each terminal to a separate power source that is isolated from the other electrode terminals. Alternatively, the electrode terminals may be connected to each other at either the proximal or distal ends of the probe to form a single wire that couples to a power source.

In one configuration, each individual electrode terminal is electrically insulated from all other electrode terminals within the probe and is connected to a power source which is isolated from each of the other electrode terminals in the array or to circuitry which limits or interrupts current flow to the electrode terminal when low resistivity material (e.g., blood, electrically conductive saline irrigant or electrically conductive gel) causes a lower impedance path between the return electrode and the individual electrode terminal. The isolated power sources for each individual electrode terminal may be separate power supply circuits having internal impedance characteristics which limit power to the associated electrode terminal when a low impedance return path is encountered. By way of example, the isolated power source may be a user selectable constant current source. In this embodiment, lower impedance paths will automatically result in lower resistive heating levels since the heating is proportional to the square of the operating current times the impedance. Alternatively, a single power source may be connected to each of the electrode terminals through independently actuatable switches, or by independent current limiting elements, such as inductors, capacitors, resistors and/or combinations thereof. The current limiting elements may be provided in the probe, connectors, cable, controller or along the conductive path from the controller to the distal tip of the probe. Alternatively, the resistance and/or capacitance may occur on the surface of the active electrode terminal(s) due to oxide layers which form selected electrode terminals (e.g., titanium or a resistive coating on the surface of metal, such as platinum).

The tip region of the probe may comprise many independent electrode terminals designed to deliver electrical energy in the vicinity of the tip. The selective application of electrical energy to the conductive fluid is achieved by connecting each individual electrode terminal and the return electrode to a power source having independently controlled or current limited channels. The return electrode(s) may comprise a single tubular member of conductive material proximal to the electrode terminal(s) at the tip which also serves as a conduit for the supply of the electrically conducting fluid between the active and return electrodes. Alternatively, the probe may comprise an array of return electrodes at the distal tip of the probe (together with the active electrodes) to maintain the electric current at the tip. The application of high frequency voltage between the return electrode(s) and the electrode array results in the generation of high electric field intensities at the distal tips of the electrode terminals with conduction of high frequency current from each individual electrode terminal to the return electrode. The current flow from each individual electrode terminal to the return electrode(s) is controlled by either active or passive means, or a combination thereof, to deliver electrical energy to the surrounding conductive fluid while minimizing energy delivery to surrounding (non-target) tissue.

The application of a high frequency voltage between the return electrode(s) and the electrode terminal(s) for appropriate time intervals effects cutting, removing, ablating, shaping, contracting or otherwise modifying the target tissue. The tissue volume over which energy is dissipated (i.e., a high current density exists) may be precisely controlled, for example, by the use of a multiplicity of small electrode terminals whose effective diameters or principal dimensions range from about 5 mm to 0.01 mm, preferably from about 2 mm to 0.05 mm, and more preferably from about 1 mm to 0.1 mm. Electrode areas for both circular and non-circular terminals will have a contact area (per electrode terminal) below 25 mm$^2$, preferably being in the range from 0.0001 mm$^2$ to 1 mm$^2$, and more preferably from 0.005 mm$^2$ to 0.5 mm$^2$. The circumscribed area of the electrode array is in the range from 0.25 mm$^2$ to 75 mm$^2$, preferably from 0.5 mm$^2$ to 40 mm$^2$, and will usually include at least two isolated electrode terminals, preferably at least five electrode terminals, often greater than 10 electrode terminals and even 50 or more electrode terminals, disposed over the distal contact surfaces on the shaft. The use of small diameter electrode terminals increases the electric field intensity and reduces the extent or depth of tissue heating as a consequence of the divergence of current flux lines which emanate from the exposed surface of each electrode terminal.

The area of the tissue treatment surface can vary widely, and the tissue treatment surface can assume a variety of geometries, with particular areas and geometries being selected for specific applications. Active electrode surfaces can have areas in the range from 0.25 mm$^2$ to 75 mm$^2$, usually being from about 0.5 mm$^2$ to 40 mm$^2$. The geometries can be planar, concave, convex, hemispherical, conical, linear "in-line" array or virtually any other regular or irregular shape. Most commonly, the active electrode(s) or electrode terminal(s) will be formed at the distal tip of the electrosurgical probe shaft, frequently being planar, disk-shaped, or hemispherical surfaces for use in reshaping procedures or being linear arrays for use in cutting. Alternatively or additionally, the active electrode(s) may be formed on lateral surfaces of the electrosurgical probe shaft (e.g., in the manner of a spatula), facilitating access to certain body structures in endoscopic procedures.

The electrically conducting fluid should have a threshold conductivity to provide a suitable conductive path between the return electrode(s) and the electrode terminal(s). The electrical conductivity of the fluid (in units of milliSiemans per centimeter or mS/cm) will usually be greater than 0.2 mS/cm, preferably will be greater than 2 mS/cm and more preferably greater than 10 mS/cm. In an exemplary embodiment, the electrically conductive fluid is isotonic saline, which has a conductivity of about 17 mS/cm.

In some embodiments, the electrode support and the fluid outlet may be recessed from an outer surface of the probe or handpiece to confine the electrically conductive fluid to the region immediately surrounding the electrode support. In addition, the shaft may be shaped so as to form a cavity around the electrode support and the fluid outlet. This helps to assure that the electrically conductive fluid will remain in contact with the electrode terminal(s) and the return electrode(s) to maintain the conductive path therebetween. In addition, this will help to maintain a vapor or plasma layer between the electrode terminal(s) and the tissue at the treatment site throughout the procedure, which reduces the thermal damage that might otherwise occur if the vapor layer were extinguished due to a lack of conductive fluid. Provision of the electrically conductive fluid around the target site also helps to maintain the tissue temperature at desired levels.

The voltage applied between the return electrode(s) and the electrode array will be at high or radio frequency, typically between about 5 kHz and 20 MHz, usually being between about 30 kHz and 2.5 MHz, preferably being between about 50 kHz and 500 kHz, more preferably less than 350 kHz, and most preferably between about 100 kHz and 200 kHz. The RMS (root mean square) voltage applied will usually be in the range from about 5 volts to 1000 volts, preferably being in the range from about 10 volts to 500 volts depending on the electrode terminal size, the operating frequency and the operation mode of the particular procedure or desired effect on the tissue (i.e., contraction, coagulation or ablation). Typically, the peak-to-peak voltage will be in the range of 10 to 2000 volts, preferably in the range of 20 to 1200 volts and more preferably in the range of about 40 to 800 volts (again, depending on the electrode size, the operating frequency and the operation mode).

As discussed above, the voltage is usually delivered in a series of voltage pulses or alternating current of time varying voltage amplitude with a sufficiently high frequency (e.g., on the order of 5 kHz to 20 MHz) such that the voltage is effectively applied continuously (as compared with e.g., lasers claiming small depths of necrosis, which are generally pulsed about 10 to 20 Hz). In addition, the duty cycle (i.e., cumulative time in any one-second interval that energy is applied) is on the order of about 50% for the present invention, as compared with pulsed lasers which typically have a duty cycle of about 0.0001%.

The preferred power source of the present invention delivers a high frequency current selectable to generate average power levels ranging from several milliwatts to tens of watts per electrode, depending on the volume of target tissue being heated, and/or the maximum allowed temperature selected for the probe tip. The power source allows the user to select the voltage level according to the specific requirements of a particular arthroscopic procedure, open surgery or other endoscopic surgery procedure. A description of a suitable power source can be found in U.S. Provisional Patent Application No. 60/062,997, filed Oct. 23, 1997, the complete disclosure of which has been incorporated herein by reference.

The power source may be current limited or otherwise controlled so that undesired heating of the target tissue or surrounding (non-target) tissue does not occur. In a presently preferred embodiment of the present invention, current limiting inductors are placed in series with each independent electrode terminal, where the inductance of the inductor is in the range of 10 uH to 50,000 uH, depending on the electrical properties of the target tissue, the desired tissue heating rate and the operating frequency. Alternatively, capacitor-inductor (LC) circuit structures may be employed, as described previously in co-pending PCT application No. PCT/US94/05168, the complete disclosure of which is incorporated herein by reference. Additionally, current limiting resistors may be selected. Preferably, these resistors will have a large positive temperature coefficient of resistance so that, as the current level begins to rise for any individual electrode terminal in contact with a low resistance medium (e.g., saline irrigant or conductive gel), the resistance of the current limiting resistor increases significantly, thereby minimizing the power delivery from said electrode terminal into the low resistance medium (e.g., saline irrigant or conductive gel).

It should be clearly understood that the invention is not limited to electrically isolated electrode terminals, or even to a plurality of electrode terminals. For example, the array of active electrode terminals may be connected to a single lead that extends through the probe shaft to a power source of high frequency current. Alternatively, the probe may incorporate a single electrode that extends directly through the probe shaft or is connected to a single lead that extends to the power source. The active electrode may have a screwdriver or conical shape as described below, or a ball shape (e.g., for tissue vaporization and desiccation), a twizzle shape (for vaporization and needle-like cutting), a spring shape (for rapid tissue debulking and desiccation), a twisted metal shape, an annular or solid tube shape or the like. Alternatively, the electrode may comprise a plurality of filaments, a rigid or flexible brush electrode (for debulking a tumor, such as a fibroid, bladder tumor or a prostate adenoma), a side-effect brush electrode on a lateral surface of the shaft, a coiled electrode or the like. In one embodiment, the probe comprises a single active electrode terminal that extends from an insulating member, e.g., ceramic, at the distal end of the probe. The insulating member is preferably a tubular structure that separates the active electrode terminal from a tubular or annular return electrode positioned proximal to the insulating member and the active electrode.

Referring to FIG. 1, an exemplary electrosurgical system 11 for cutting, ablating or resecting tissue will now be described in detail. Electrosurgical system 11 generally comprises an electrosurgical handpiece or probe 10 connected to a power supply 28 for providing high frequency voltage to a target site and a fluid source 21 for supplying electrically conducting fluid 50 to probe 10. In addition, electrosurgical system 11 may include an endoscope (not shown) with a fiber optic head light for viewing the surgical site, particularly in sinus procedures or procedures in the ear or the back of the mouth. The endoscope may be integral with probe 10, or it may be part of a separate instrument. The system 11 may also include a vacuum source (not shown) for coupling to a suction lumen or tube 211 (see FIG. 2) in the probe 10 for aspirating the target site.

As shown, probe 10 generally includes a proximal handle 19 and an elongate shaft 18 having a linear array 12 of electrode terminals 58 at its distal end. A connecting cable 34 has a connector 26 for electrically coupling the electrode terminals 58 to power supply 28. The electrode terminals 58 are electrically isolated from each other and each of the terminals 58 is connected to an active or passive control network within power supply 28 by means of a plurality of individually insulated conductors (not shown). A fluid supply tube 15 is connected to a fluid tube 14 of probe 10 for supplying electrically conducting fluid 50 to the target site.

Power supply 28 has an operator controllable voltage level adjustment 30 to change the applied voltage level, which is observable at a voltage level display 32. Power supply 28 also includes first, second and third foot pedals 37, 38, 39 and a cable 36 which is removably coupled to power supply 28. The foot pedals 37, 38, 39 allow the surgeon to remotely adjust the energy level applied to electrode terminals 58. In an exemplary embodiment, first foot pedal 37 is used to place the power supply into the "ablation" mode and second foot pedal 38 places power supply 28 into the "coagulation" mode. The third foot pedal 39 allows the user to adjust the voltage level within the "ablation" mode. In the ablation mode, a sufficient voltage is applied to the electrode terminals to establish the requisite conditions for molecular dissociation of the tissue (i.e., vaporizing a portion of the electrically conductive fluid, ionizing charged particles within the vapor layer and accelerating these charged particles against the tissue). As discussed above, the requisite voltage level for ablation will vary depending on the number, size, shape and spacing of the electrodes, the distance in which the electrodes extend from the support member, etc. Once the surgeon places the power supply in the "ablation" mode, voltage level adjustment 30 or third foot pedal 39 may be used to adjust the voltage level to adjust the degree or aggressiveness of the ablation.

Of course, it will be recognized that the voltage and modality of the power supply may be controlled by other input devices. However, applicant has found that foot pedals are convenient methods of controlling the power supply while manipulating the probe during a surgical procedure.

In the coagulation mode, the power supply 28 applies a low enough voltage to the electrode terminals (or the coagulation electrode) to avoid vaporization of the electrically conductive fluid and subsequent molecular dissociation of the tissue. The surgeon may automatically toggle the power supply between the ablation and coagulation modes by alternatively stepping on foot pedals 37, 38, respectively. This allows the surgeon to quickly move between coagulation and ablation in situ, without having to remove his/her concentration from the surgical field or without having to request an assistant to switch the power supply. By way of example, as the surgeon is sculpting soft tissue in the ablation mode, the probe typically will simultaneously seal and/or coagulation small severed vessels within the tissue. However, larger vessels, or vessels with high fluid pressures (e.g., arterial vessels) may not be sealed in the ablation mode. Accordingly, the surgeon can simply step on foot pedal 38, automatically lowering the voltage level below the threshold level for ablation, and apply sufficient pressure onto the severed vessel for a sufficient period of time to seal and/or coagulate the vessel. After this is completed, the surgeon may quickly move back into the ablation mode by stepping on foot pedal 37. A specific design of a suitable power supply for use with the present invention can be found in provisional patent application No. 60/062,997, filed Oct. 23, 1997, previously incorporated herein by reference.

Figure 2:
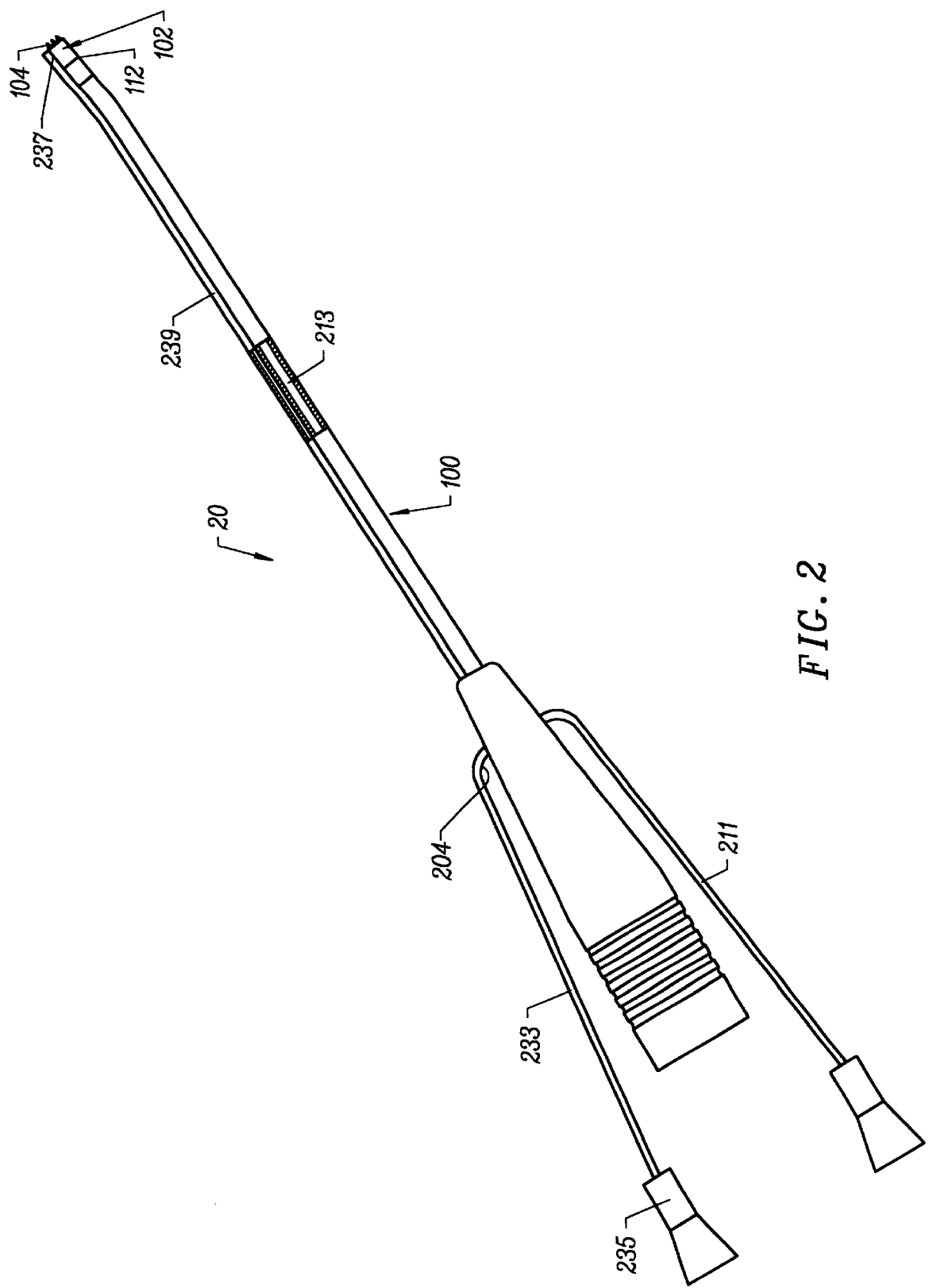
FIG. 2 is a side view of an electrosurgical probe according to the present invention.

FIGS. 2–5 illustrate an exemplary electrosurgical probe 20 constructed according to the principles of the present invention. Electrosurgical probe 20 is particularly useful for cutting tissue in the region of the head and neck, e.g., the ear, nose and throat, of a patient. However, it will be recognized that probe 20, or a similar device, may be used in a variety of applications, as discussed above. As shown in FIG. 2, probe 20 generally includes an elongated shaft 100 which may be flexible or rigid, a handle 204 coupled to the proximal end of shaft 100 and an electrode support member 102 coupled to the distal end of shaft 100. Shaft 100 preferably comprises a plastic material that is easily molded into the shape shown in FIG. 3. In an alternative embodiment (not shown), shaft 100 comprises an electrically conducting material, usually metal, which is selected from the group comprising tungsten, stainless steel alloys, platinum or its alloys, titanium or its alloys, molybdenum or its alloys, and nickel or its alloys. In this embodiment, shaft 100 includes an electrically insulating jacket 108, which is typically formed as one or more electrically insulating sheaths or coatings, such as polytetrafluoroethylene, polyimide, and the like. The provision of the electrically insulating jacket over the shaft prevents direct electrical contact between these metal elements and any adjacent body structure or the surgeon. Such direct electrical contact between a body structure (e.g., tendon) and an exposed electrode could result in unwanted heating and necrosis of the structure at the point of contact causing necrosis.

Handle 204 typically comprises a plastic material that is easily molded into a suitable shape for handling by the surgeon. Handle 204 defines an inner cavity (not shown) that houses the electrical connections 250 (FIG. 5), and provides a suitable interface for connection to an electrical connecting cable 22 (see FIG. 2). Electrode support member 102 extends from the distal end of shaft 100 (usually about 1 to 20 mm), and provides support for a plurality of electrically isolated electrode terminals 104 (see FIG. 4B). As shown in FIG. 2, a fluid tube 233 extends through an opening in handle 204, and includes a connector 235 for connection to a fluid supply source, for supplying electrically conductive fluid to the target site. Fluid tube 233 is coupled to a distal fluid tube 239 that extends along the outer surface of shaft 100 to an opening 237 at the distal end of the probe 20, as discussed in detail below. Of course, the invention is not limited to this configuration. For example, fluid tube 233 may extend through a single lumen (not shown) in shaft 100, or it may be coupled to a plurality of lumens (also not shown) that extend through shaft 100 to a plurality of openings at its distal end. Probe 20 may also include a valve 17 (FIG. 2) or equivalent structure for controlling the flow rate of the electrically conducting fluid to the target site.

Figure 3:
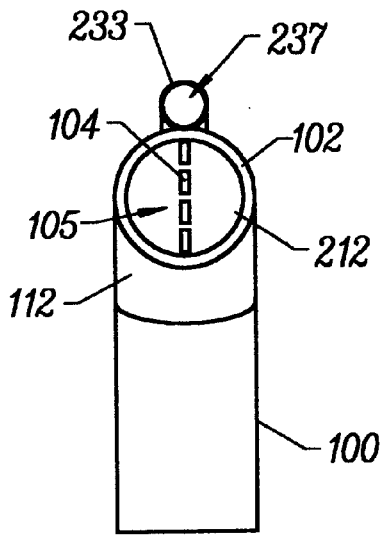
FIG. 3 is an end view of the probe of FIG. 2.
Figure 4:
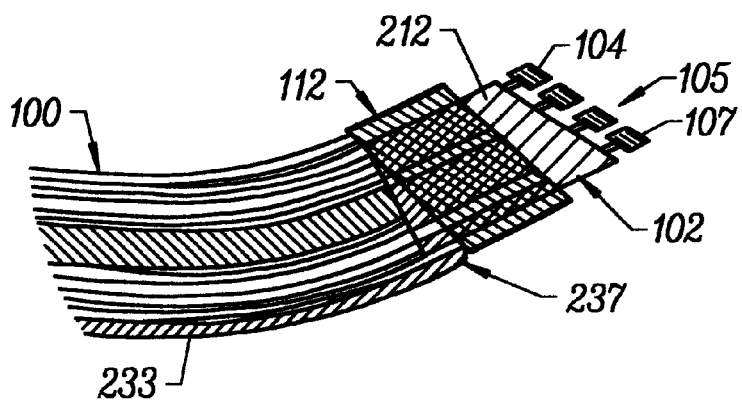
FIG. 4 is a cross sectional view of the electrosurgical probe of FIG. 1.

As shown in FIGS. 3 and 4, electrode support member 102 has a substantially planar tissue treatment surface 212 and comprises a suitable insulating material (e.g., ceramic or glass material, such as alumina, zirconia and the like) which could be formed at the time of manufacture in a flat, hemispherical or other shape according to the requirements of a particular procedure. The preferred support member material is alumina, available from Kyocera Industrial Ceramics Corporation, Elkgrove, Ill., because of its high thermal conductivity, good electrically insulative properties, high flexural modulus, resistance to carbon tracking, biocompatibility, and high melting point. The support member 102 is adhesively joined to a tubular support member (not shown) that extends most or all of the distance between support member 102 and the proximal end of probe 20. The tubular member preferably comprises an electrically insulating material, such as an epoxy or silicone-based material.

In a preferred construction technique, electrode terminals 104 extend through pre-formed openings in the support member 102 so that they protrude above tissue treatment surface 212 by the desired distance. The electrodes are then bonded to the tissue treatment surface 212 of support member 102, typically by an inorganic sealing material. The sealing material is selected to provide effective electrical insulation, and good adhesion to both the alumina member 102 and the platinum or titanium electrode terminals 104. The sealing material additionally should have a compatible thermal expansion coefficient and a melting point well below that of platinum or titanium and alumina or zirconia, typically being a glass or glass ceramic In the embodiment shown in FIGS. 2–5, probe 20 includes a return electrode 112 for completing the current path between electrode terminals 104 and a high frequency power supply 28 (see FIG. 1). As shown, return electrode 112 preferably comprises an annular conductive band coupled to the distal end of shaft 100 slightly proximal to tissue treatment surface 212 of electrode support member 102, typically about 0.5 to 10 mm and more preferably about 1 to 10 mm. Return electrode 112 is coupled to a connector 258 that extends to the proximal end of probe 10, where it is suitably connected to power supply 28 (FIG. 1).

As shown in FIG. 2, return electrode 112 is not directly connected to electrode terminals 104. To complete this current path so that electrode terminals 104 are electrically connected to return electrode 112, electrically conducting fluid (e.g., isotonic saline) is caused to flow therebetween. In the representative embodiment, the electrically conducting fluid is delivered through an external fluid tube 239 to opening 237, as described above. Alternatively, the fluid may be delivered by a fluid delivery element (not shown) that is separate from probe 20. In arthroscopic procedures, for example, the joint cavity is typically flooded with isotonic saline and the probe 20 will be introduced into this flooded cavity. Electrically conducting fluid will be continually resupplied with a separate instrument to maintain the conduction path between return electrode 112 and electrode terminals 104.

In alternative embodiments, the fluid path may be formed in probe 20 by, for example, an inner lumen or an annular gap between the return electrode and a tubular support member within shaft 100 (not shown). This annular gap may be formed near the perimeter of the shaft 100 such that the electrically conducting fluid tends to flow radially inward towards the target site, or it may be formed towards the center of shaft 100 so that the fluid flows radially outward. In both of these embodiments, a fluid source (e.g., a bag of fluid elevated above the surgical site or having a pumping device), is coupled to probe 90 via a fluid supply tube (not shown) that may or may not have a controllable valve. A more complete description of an electrosurgical probe incorporating one or more fluid lumen(s) can be found in parent application U.S. Pat. No. 5,697,281, filed on Jun. 7, 1995, the complete disclosure of which has previously been incorporated herein by reference.

Referring to FIG. 3, the electrically isolated electrode terminals 104 are preferably spaced from each other and aligned to form a linear array 105 of electrodes for cutting a substantially linear incision in the tissue. The tissue treatment surface and individual electrode terminals 104 will usually have dimensions within the ranges set forth above. Electrode terminals 104 preferably have a distal edge 107 to increase the electric field intensities around terminals 104, and to facilitate cutting of tissue. Thus, electrode terminals 104 have a screwdriver shape in the representative embodiment of FIGS. 2–5. In the representative embodiment, the tissue treatment surface 212 has a circular cross-sectional shape with a diameter in the range of about 1 mm to 30 mm, usually about 2 to 20 mm. The individual electrode terminals 104 preferably extend outward from tissue treatment surface 212 by a distance of about 0.1 to 8 mm, usually about 1 to 4 mm. Applicant has found that this configuration increases the high electric field intensities and associated current densities around electrode terminals 104 to facilitate the ablation of tissue as described in detail above.

The probe may include a suction or aspiration lumen 213 (see FIG. 2) within shaft 100 and a suction tube 211 (FIG. 2) for aspirating tissue, fluids and/or gases from the target site. In this embodiment, the electrically conductive fluid generally flows from opening 237 of fluid tube 239 radially inward and then back through one or more openings (not shown) in support member 102. Aspirating the electrically conductive fluid during surgery allows the surgeon to see the target site, and it prevents the fluid from flowing into the patient's body, e.g., into the spine, the abdomen or the thoracic cavity. This aspiration should be controlled, however, so that the conductive fluid maintains a conductive path between the active electrode terminal(s) and the return electrode. In some embodiments, the probe 20 will also include one or more aspiration electrode(s) (not shown) coupled to the aspiration lumen for inhibiting clogging during aspiration of tissue fragments from the surgical site. A more complete description of these embodiments can be found in commonly assigned co-pending application entitled "Systems and Methods for Tissue Resection, Ablation and Aspiration", filed Jan. 19, 1998, Ser. No. 09/010,382, the complete disclosure of which is incorporated herein by reference for all purposes.

Figure 5:
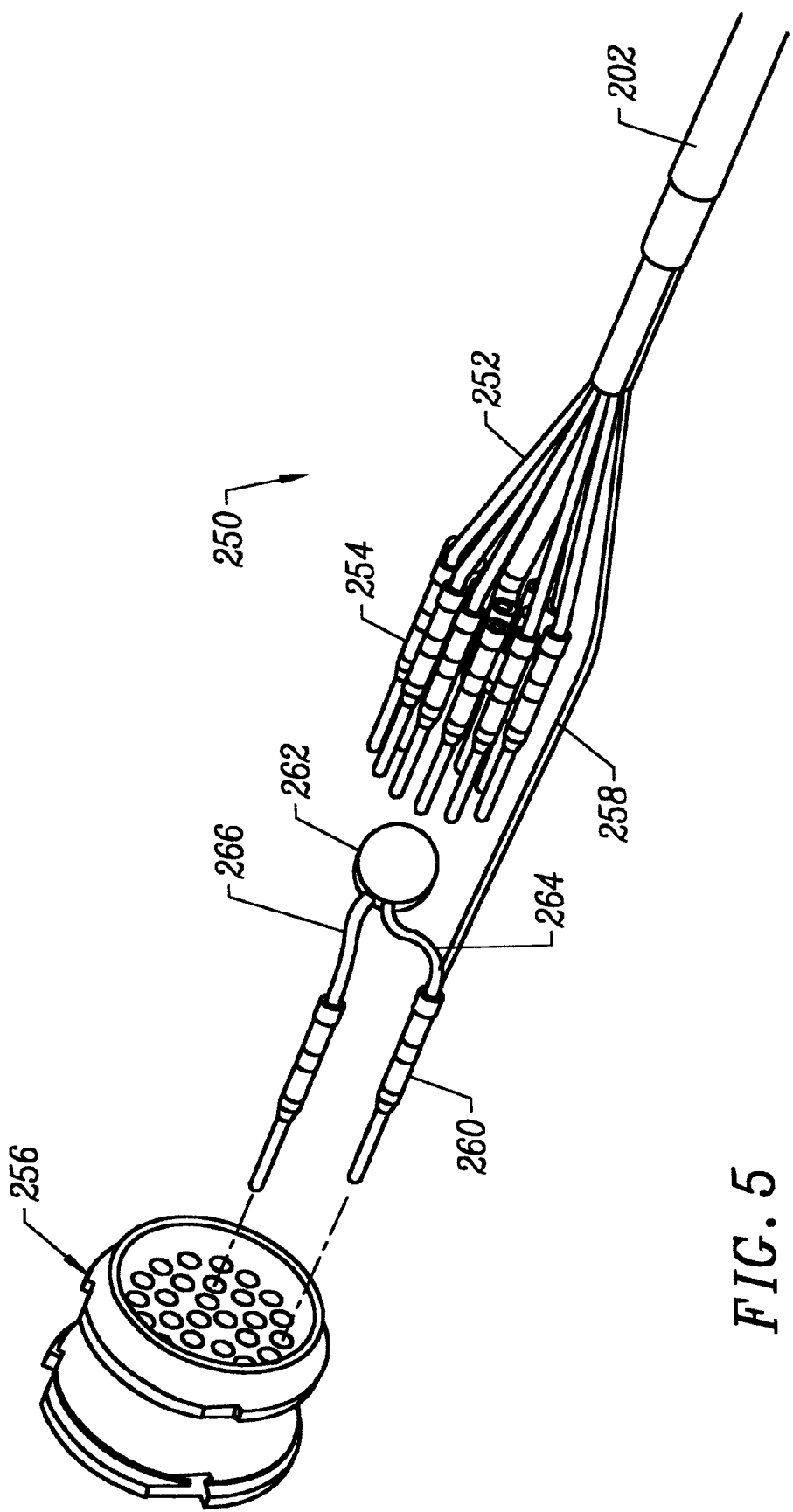
FIG. 5 is an exploded view of a proximal portion of the electrosurgical probe.

FIG. 5 illustrates the electrical connections 250 within handle 204 for coupling electrode terminals 104 and return electrode 112 to the power supply 28. As shown, a plurality of wires 252 extend through shaft 100 to couple terminals 104 to a plurality of pins 254, which are plugged into a connector block 256 for coupling to a connecting cable 22 (FIG. 1). Similarly, return electrode 112 is coupled to connector block 256 via a wire 258 and a plug 260.

According to the present invention, the probe 90 further includes an identification element that is characteristic of the particular electrode assembly so that the same power supply 28 can be used for different electrosurgical operations. In one embodiment, for example, the probe 90 includes a voltage reduction element or a voltage reduction circuit for reducing the voltage applied between the electrode terminals 104 and the return electrode 112. The voltage reduction element serves to reduce the voltage applied by the power supply so that the voltage between the electrode terminals and the return electrode is low enough to avoid excessive power dissipation into the electrically conducting medium and/or ablation of the soft tissue at the target site. The voltage reduction element primarily allows the electrosurgical probe 90 to be compatible with other ArthroCare generators that are adapted to apply higher voltages for ablation or vaporization of tissue. For contraction of tissue, for example, the voltage reduction element will serve to reduce a voltage of about 100 to 135 volts rms (which is a setting of 1 on the ArthroCare Model 970 and 980 (i.e., 2000) Generators) to about 45 to 60 volts rms, which is a suitable voltage for contraction of tissue without ablation (e.g., molecular dissociation) of the tissue.

Of course, for some procedures, such as endoscopic sinus surgery, the probe will typically not require a voltage reduction element. Alternatively, the probe may include a voltage increasing element or circuit, if desired.

In the representative embodiment, the voltage reduction element is a dropping capacitor 262 which has first leg 264 coupled to the return electrode wire 258 and a second leg 266 coupled to connector block 256. Of course, the capacitor may be located in other places within the system, such as in, or distributed along the length of, the cable, the generator, the connector, etc. In addition, it will be recognized that other voltage reduction elements, such as diodes, transistors, inductors, resistors, capacitors or combinations thereof, may be used in conjunction with the present invention. For example, the probe 90 may include a coded resistor (not shown) that is constructed to lower the voltage applied between return electrode 112 and electrode terminals 104 to a suitable level for contraction of tissue. In addition, electrical circuits may be employed for this purpose.

Alternatively or additionally, the cable 22 that couples the power supply 10 to the probe 90 may be used as a voltage reduction element. The cable has an inherent capacitance that can be used to reduce the power supply voltage if the cable is placed into the electrical circuit between the power supply, the electrode terminals and the return electrode. In this embodiment, the cable 22 may be used alone, or in combination with one of the voltage reduction elements discussed above, e.g., a capacitor.

Further, it should be noted that the present invention can be used with a power supply that is adapted to apply a voltage within the selected range for treatment of tissue. In this embodiment, a voltage reduction element or circuitry may not be desired.

Figure 6A:
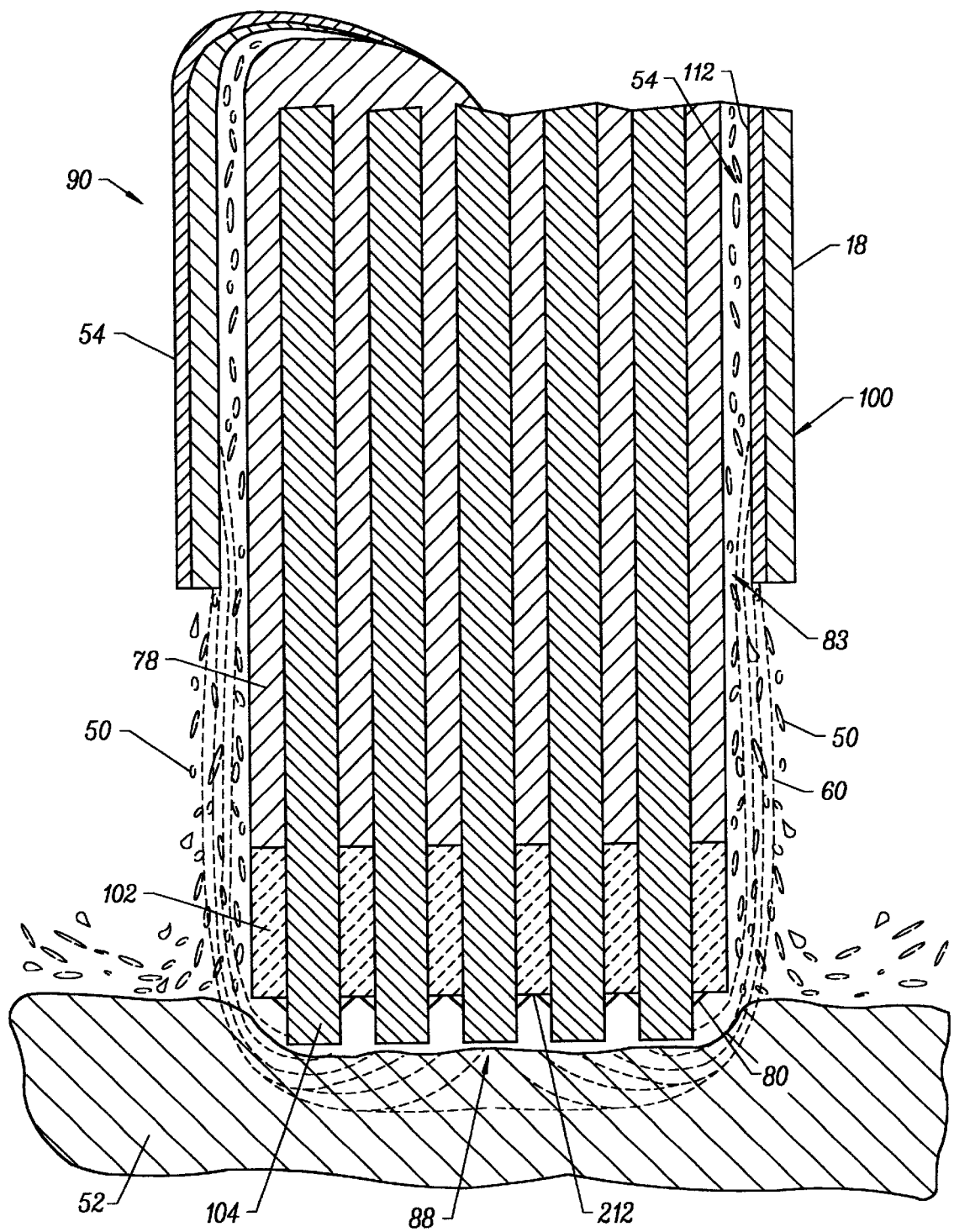
FIGS. 6A–6C are cross-sectional views of the distal portions of three different embodiments of an electrosurgical probe according to the present invention.
Figure 6B:
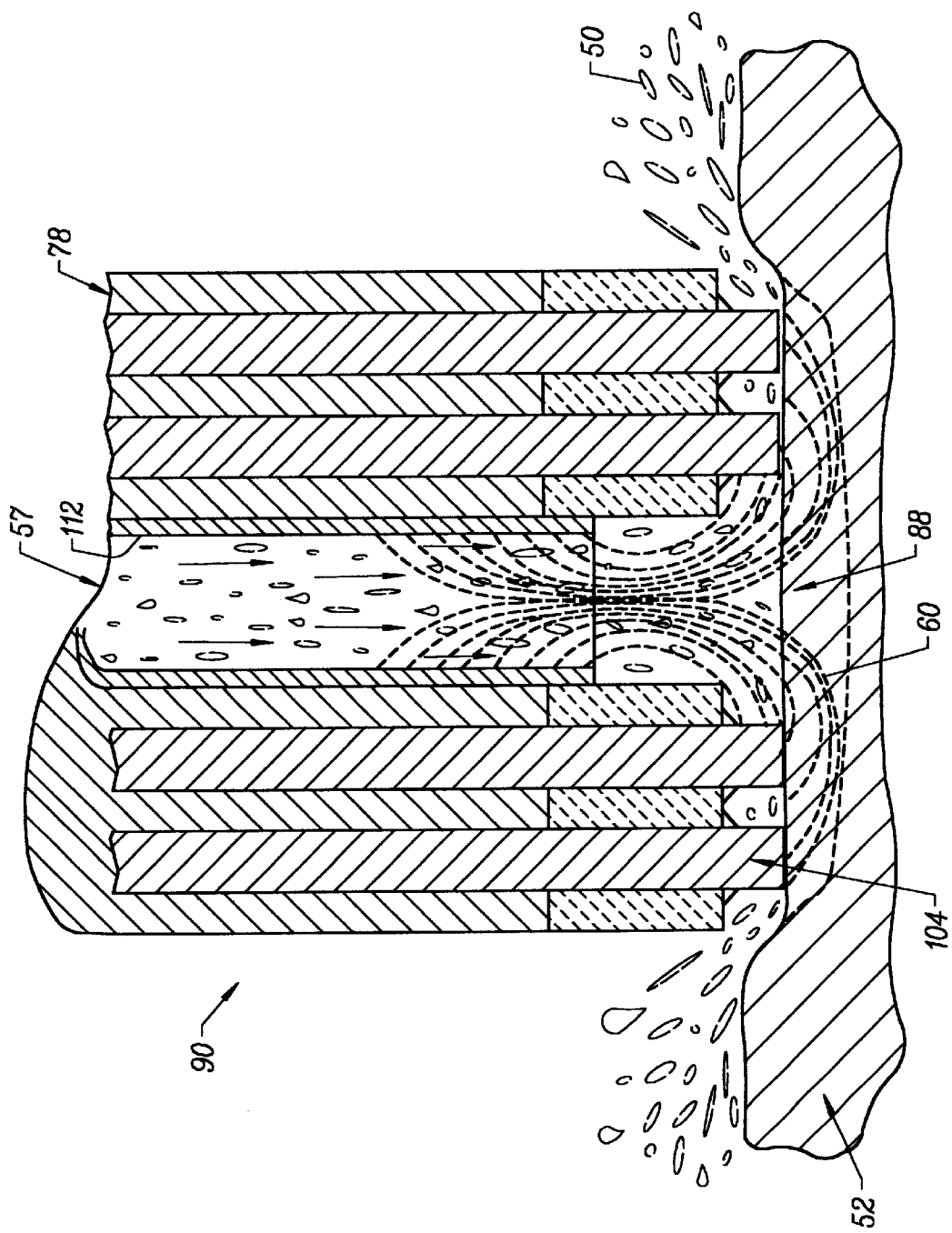
Figure 6C:
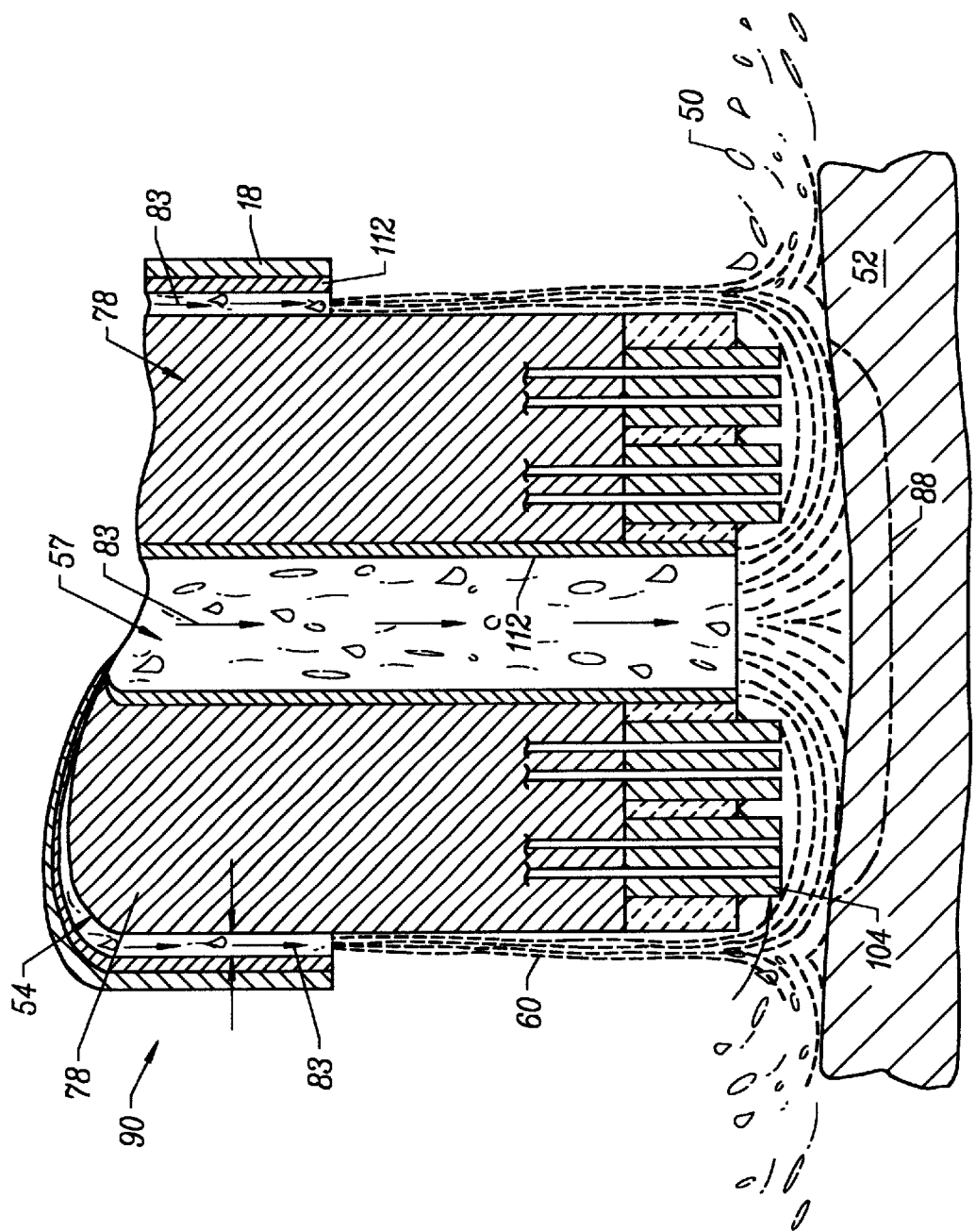

FIGS. 6A–6C schematically illustrate the distal portion of three different embodiments of probe 90 according to the present invention. As shown in 6A, electrode terminals 104 are anchored in a support matrix 102 of suitable insulating material (e.g., ceramic or glass material, such as alumina, zirconia and the like) which could be formed at the time of manufacture in a flat, hemispherical or other shape according to the requirements of a particular procedure. The preferred support matrix material is alumina, available from Kyocera Industrial Ceramics Corporation, Elkgrove, Ill., because of its high thermal conductivity, good electrically insulative properties, high flexural modulus, resistance to carbon tracking, biocompatibility, and high melting point. The support matrix 102 is adhesively joined to a tubular support member 78 that extends most or all of the distance between matrix 102 and the proximal end of probe 90. Tubular member 78 preferably comprises an electrically insulating material, such as an epoxy or silicone-based material.

In a preferred construction technique, electrode terminals 104 extend through pre-formed openings in the support matrix 102 so that they protrude above tissue treatment surface 212 by the desired distance. The electrodes are then bonded to the tissue treatment surface 212 of support matrix 102, typically by an inorganic sealing material 80. Sealing material 80 is selected to provide effective electrical insulation, and good adhesion to both the alumina matrix 102 and the platinum or titanium electrode terminals. Sealing material 80 additionally should have a compatible thermal expansion coefficient and a melting point well below that of platinum or titanium and alumina or zirconia, typically being a glass or glass ceramic.

In the embodiment shown in FIG. 6A, return electrode 112 comprises an annular member positioned around the exterior of shaft 100 of probe 90. Return electrode 112 may fully or partially circumscribe tubular support member 78 to form an annular gap 54 therebetween for flow of electrically conducting liquid 50 therethrough, as discussed below. Gap 54 preferably has a width in the range of 0.25 mm to 4 mm. Alternatively, probe may include a plurality of longitudinal ribs between support member 78 and return electrode 112 to form a plurality of fluid lumens extending along the perimeter of shaft 100. In this embodiment, the plurality of lumens will extend to a plurality of openings.

Return electrode 112 is disposed within an electrically insulative jacket 18, which is typically formed as one or more electrically insulative sheaths or coatings, such as polytetrafluoroethylene, polyamide, and the like. The provision of the electrically insulative jacket 18 over return electrode 112 prevents direct electrical contact between return electrode 56 and any adjacent body structure. Such direct electrical contact between a body structure (e.g., tendon) and an exposed electrode member 112 could result in unwanted heating and necrosis of the structure at the point of contact causing necrosis.

As shown in FIG. 6A, return electrode 112 is not directly connected to electrode terminals 104. To complete this current path so that terminals 104 are electrically connected to return electrode 112, electrically conducting liquid 50 (e.g., isotonic saline) is caused to flow along fluid path(s) 83. Fluid path 83 is formed by annular gap 54 between outer return electrode 112 and tubular support member. The electrically conducting liquid 50 flowing through fluid path 83 provides a pathway for electrical current flow between electrode terminals 104 and return electrode 112, as illustrated by the current flux lines 60 in FIG. 6A. When a voltage difference is applied between electrode terminals 104 and return electrode 112, high electric field intensities will be generated at the distal tips of terminals 104 with current flow from terminals 104 through the target tissue to the return electrode, the high electric field intensities causing ablation of tissue 52 in zone 88.

FIG. 6B illustrates another alternative embodiment of electrosurgical probe 90 which has a return electrode 112 positioned within tubular member 78. Return electrode 112 is preferably a tubular member defining an inner lumen 57 for allowing electrically conducting liquid 50 (e.g., isotonic saline) to flow therethrough in electrical contact with return electrode 112. In this embodiment, a voltage difference is applied between electrode terminals 104 and return electrode 112 resulting in electrical current flow through the electrically conducting liquid 50 as shown by current flux lines 60 (FIG. 3). As a result of the applied voltage difference and concomitant high electric field intensities at the tips of electrode terminals 104, tissue 52 becomes ablated or transected in zone 88.

FIG. 6C illustrates another embodiment of probe 90 that is a combination of the embodiments in FIGS. 6A and 6B. As shown, this probe includes both an inner lumen 57 and an outer gap or plurality of outer lumens 54 for flow of electrically conductive fluid. In this embodiment, the return electrode 112 may be positioned within tubular member 78 as in FIG. 6B, outside of tubular member 78 as in FIG. 6A, or in both locations.

Figure 8:
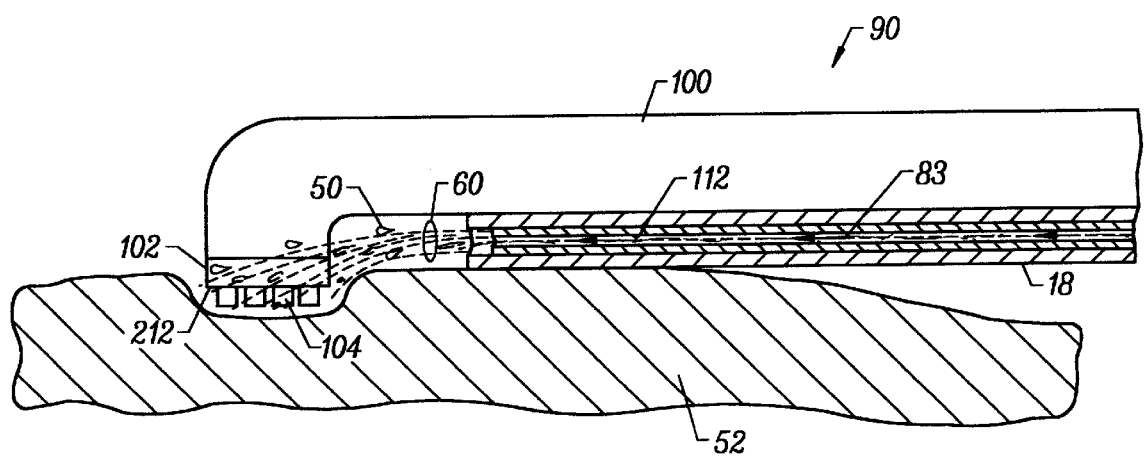
FIG. 8 illustrates an electrosurgical probe with a 90° distal bend and a lateral fluid lumen.

FIG. 8 illustrates another embodiment of probe 90 where the distal portion of shaft 100 is bent so that electrode terminals extend transversely to the shaft. Preferably, the distal portion of shaft 100 is perpendicular to the rest of the shaft so that tissue treatment surface 212 is generally parallel to the shaft axis. In this embodiment, return electrode 112 is mounted to the outer surface of shaft 100 and is covered with an electrically insulating jacket 18. The electrically conducting fluid 50 flows along flow path 83 through return electrode 112 and exits the distal end of electrode 112 at a point proximal of tissue treatment surface 212. The fluid is directed exterior of shaft to surface 212 to create a return current path from electrode terminals 104, through the fluid 50, to return electrode 12, as shown by current flux lines 60.

Figure 9:
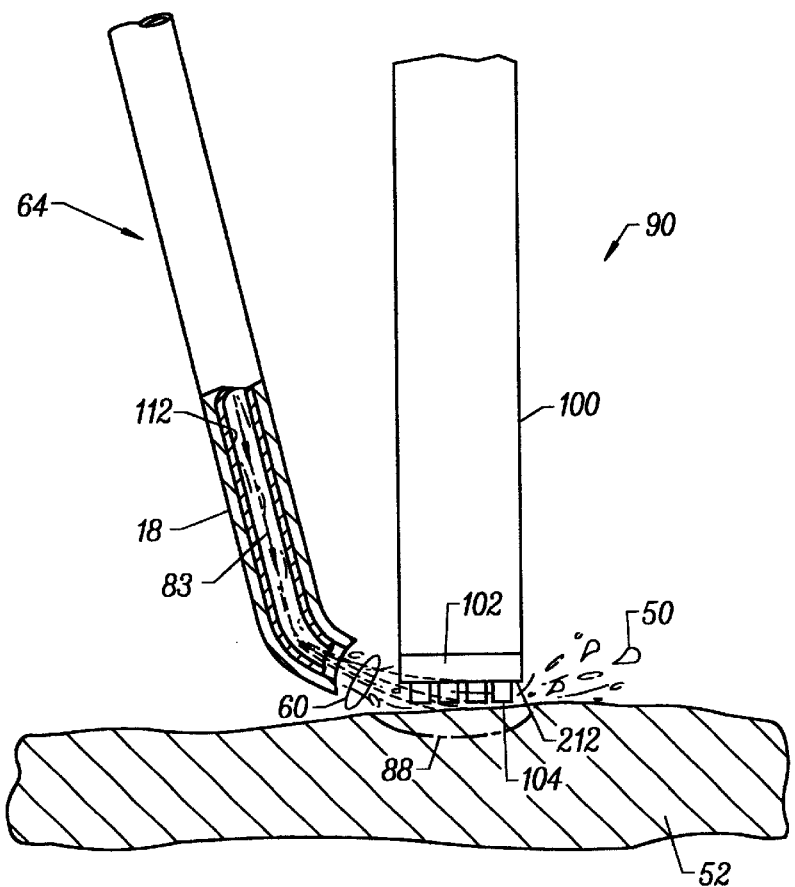
FIG. 9 illustrates an electrosurgical system with a separate fluid delivery instrument according to the present invention.

FIG. 9 illustrates another embodiment of the invention where electrosurgical system 11 further includes a liquid supply instrument 64 for supplying electrically conducting fluid 50 between electrode terminals 104 and return electrode 112. Liquid supply instrument 64 comprises an inner tubular member or return electrode 112 surrounded by an electrically insulating jacket 18. Return electrode 112 defines an inner passage 83 for flow of fluid 50. As shown in FIG. 9, the distal portion of instrument 64 is preferably bent so that liquid 50 is discharged at an angle with respect to instrument 64. This allows the surgical team to position liquid supply instrument 64 adjacent tissue treatment surface 212 with the proximal portion of supply instrument 64 oriented at a similar angle to probe 90.

Figure 7A:
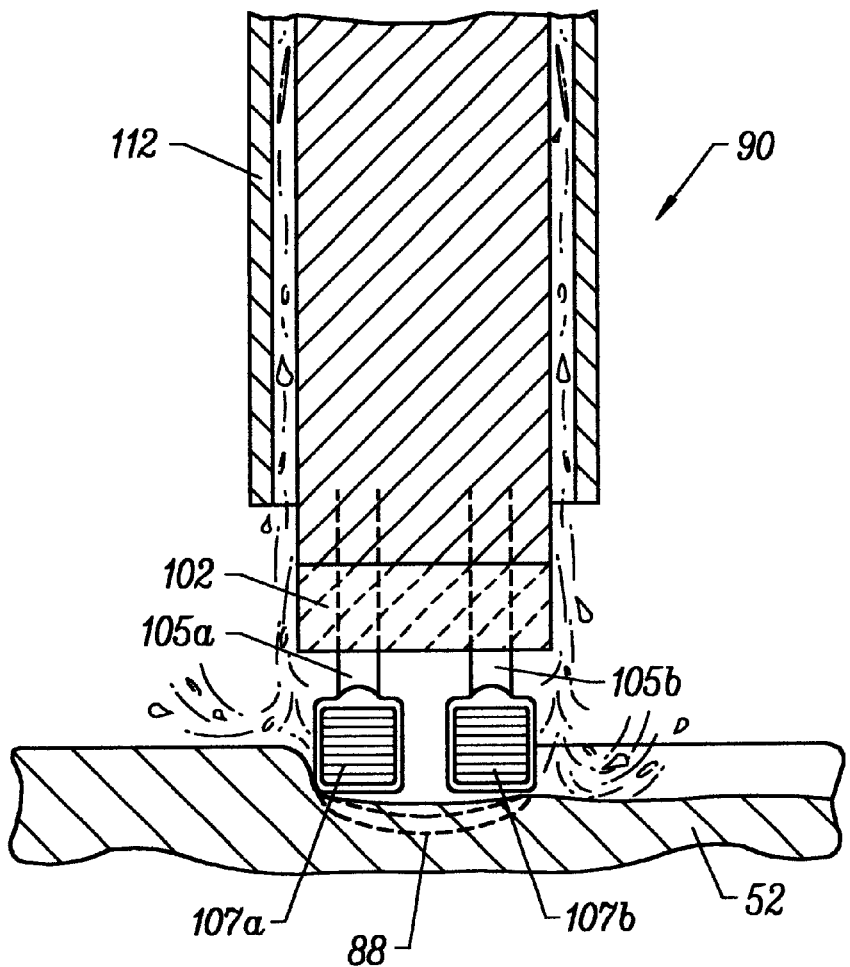
FIGS. 7A and 7B are cross-sectional and end views, respectively, of yet another electrosurgical probe incorporating flattened electrode terminals.
Figure 7B:
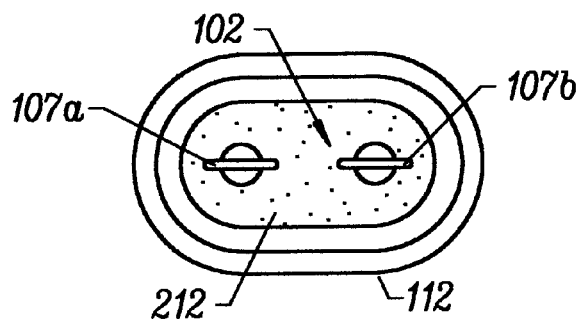

The present invention is not limited to an electrode array disposed on a relatively planar surface at the distal tip of probe 90, as described above. Referring to FIGS. 7A and 7B, an alternative probe 90 includes a pair of electrodes 105a, 105b mounted to the distal end of shaft 100. Electrodes 105a, 105b are electrically connected to power supply as described above and preferably have tips 107a, 107b with a screwdriver shape. The screwdriver shape provides a greater amount of "edges" to electrodes 105a, 105b, to increase the electric field intensity and current density at the edges and thereby improve the cutting ability as well as the ability to limit bleeding from the incised tissue (i.e., hemostasis).

FIG. 10 illustrates yet another embodiment designed for cutting of body structures. In this embodiment, the electrode terminals 104 are arranged in a linear or columnar array of one or more closely spaced columns so that as the electrodes 104 are moved along the longer axis (denoted by arrow 160 in FIG. 10), the current flux lines are narrowly confined at the tip of the electrode terminals 104 and result in a cutting effect in the body structure being treated. As before, the current flux lines 60 emanating from the electrode terminals 104 pass through the electrically conducting liquid to the return electrode structure 112 located proximal to the probe tip.

Referring now to FIGS. 11 and 12, alternative geometries are shown for the electrode terminals 104. These alternative electrode geometries allow the electrical current densities emanating from the electrode terminals 104 to be concentrated to achieve an increased ablation rate and/or a more concentrated ablation effect due to the fact that sharper edges (i.e., regions of smaller radii of curvature) result in higher current densities. FIG. 11 illustrates a flattened extension of a round wire electrode terminal 104 which results in higher current densities at the edges 180. Another example is shown in FIG. 12 in which the electrode terminal 104 is formed into a cone shaped point 182 resulting in higher current densities at the tip of the cone.

Figure 14A:
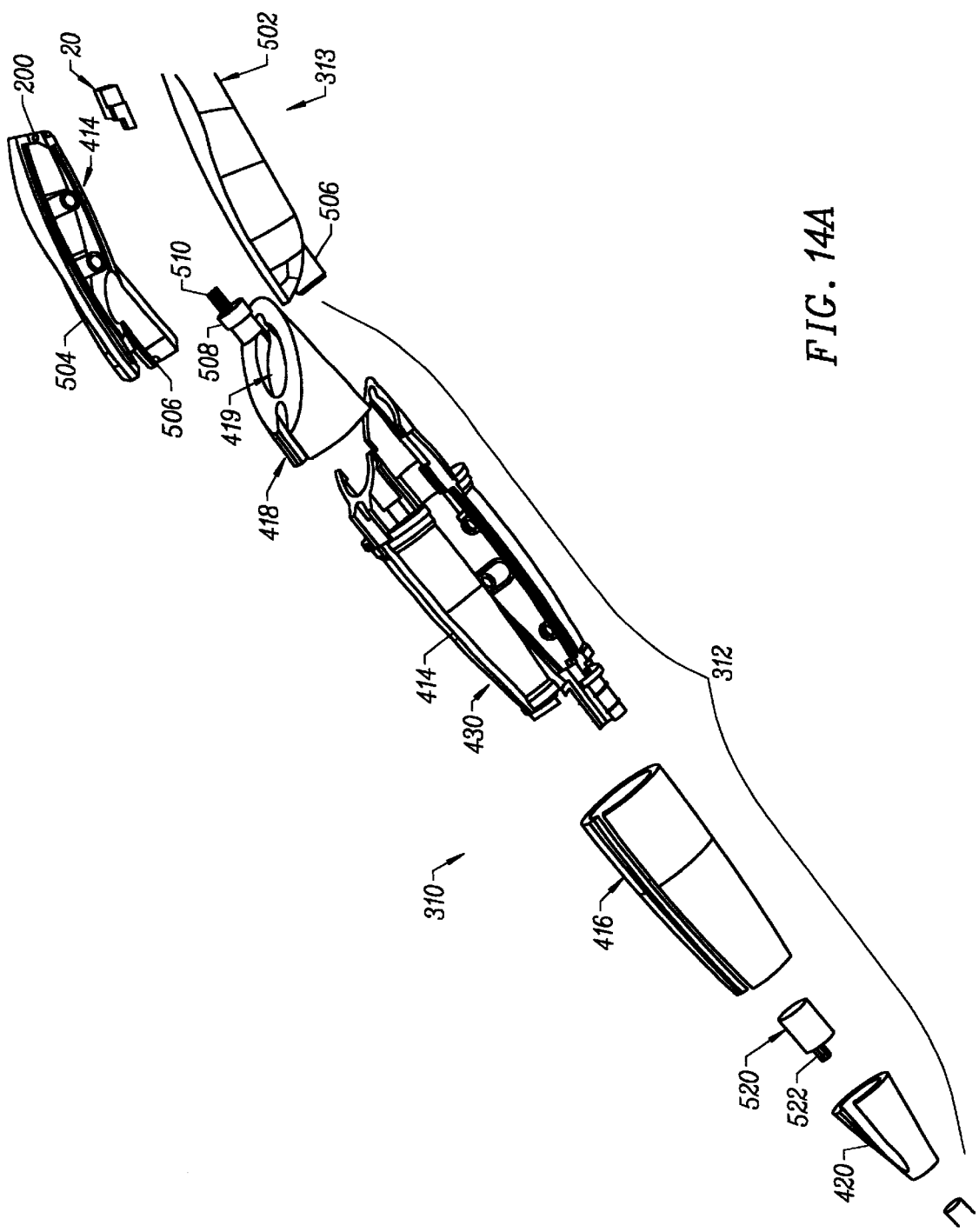
FIGS. 14A–14C are exploded, isometric views of the probe of FIG. 13.
Figure 14B:
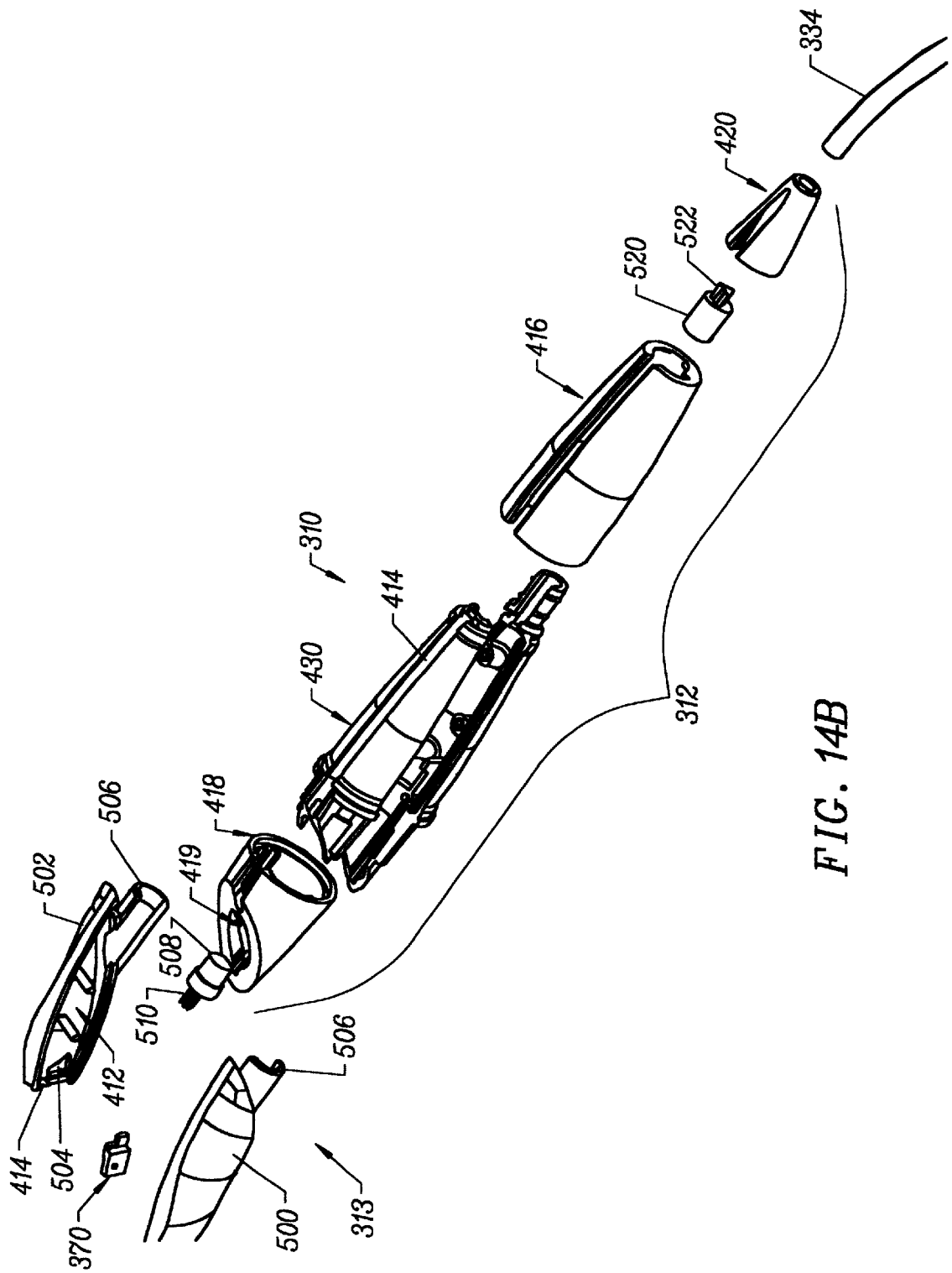
Figure 14C:
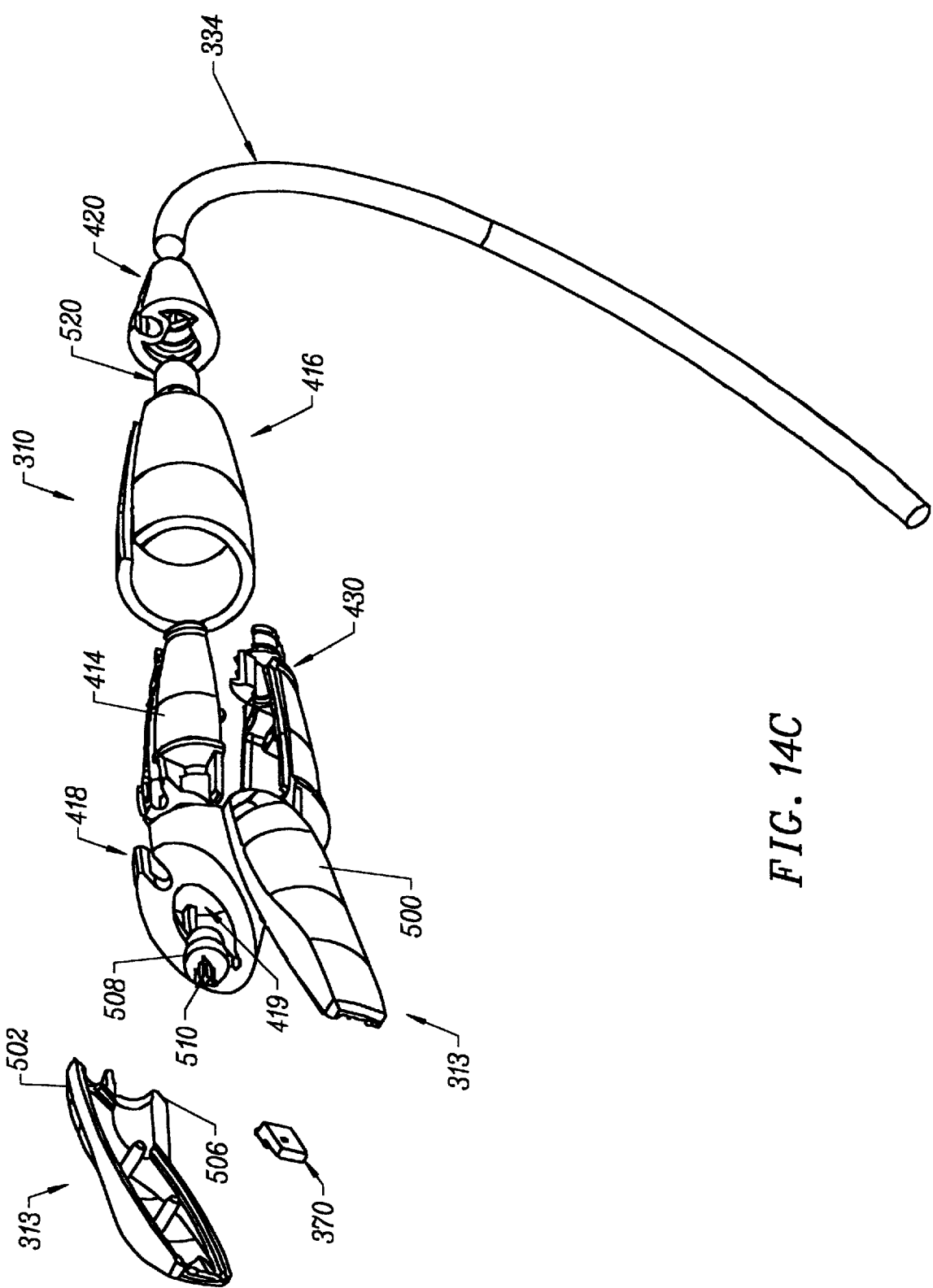
Figure 15:
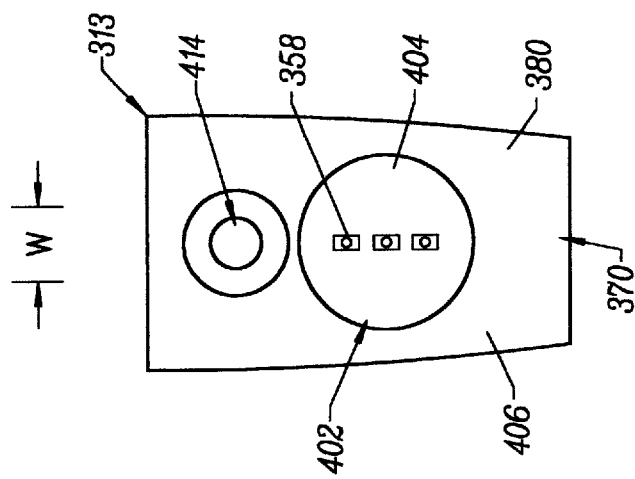
FIG. 15 is an end view of the distal tip of the probe, illustrating an electrode support with a plurality of electrode terminals.

FIGS. 13–16 illustrate an exemplary electrosurgical probe 300 or "dermal scalpel" for cutting and removing structures from the outer surface of the skin, such as lesions, scars, etc. Probe 300 comprises a shaft or disposable tip 313 removably coupled to a proximal handle 312, and an electrically insulating electrode support member 370 extending from tip 313 for supporting a plurality of electrode terminals 358 (see FIGS. 13 and 16). Tip 313 and handle 312 typically comprise a plastic material that is easily molded into a suitable shape for handling by the surgeon. As shown in FIGS. 15 and 17, handle 312 defines an inner cavity 372 that houses the electrical connections 374, and provides a suitable interface for connection to electrical connecting cable 34 (see FIG. 1). In the exemplary embodiment, handle 312 is constructed of a steam autoclavable plastic or metal (e.g., polyethylether keytone, or a stable metal alloy containing aluminum and/or zine. so that it can be re-used by sterilizing handle 312 between surgical procedures. High service temperature materials are preferred, such as a silicone cable jacket and a poly-ether-imide handpiece or ULTEM® that can withstand a repeated exposure to high temperatures.

Referring to FIGS. 14A–14C, tip 313 preferably comprises first and second housing halves 500, 502 that snap fit together, and form a recess 404 therebetween for holding electrode support member 370 within the tip 313. Electrode support member 370 extends from the distal end of tip 313 (usually about 0.5 to 20 mm), and provides support for a plurality of electrically isolated electrode terminals 358 and one or more return electrodes 400 (see FIG. 16). Alternatively, electrode support member 370 may be recessed from the distal end of tip 313 to help confine the electrically conductive fluid around the electrode terminals 358 during the surgical procedure, as discussed above. Electrode support member 370 has a substantially planar tissue treatment surface 380 that is usually disposed at an angle of about 10 to 90 degrees relative to the longitudinal axis of handle 312 to facilitate handling by the surgeon. In the exemplary embodiment, this function is accomplished by orienting tip 313 at an acute angle relative to the longitudinal axis of handle 312.

In the embodiment shown in FIGS. 13–16, probe 310 includes a single annular return electrode 400 for completing the current path between electrode terminals 358 and power supply 328 (see FIG. 1). As shown, return electrode 400 preferably has a fluid contact surface slightly proximal to tissue treatment surface 380, typically about 0.1 to 2 mm, preferably about 0.2 to 1 mm. Return electrode 400 is coupled to a connector 404 that extends to the proximal end of handle 313, where it is suitably connected to power supply 28 (FIG. 1).

Referring to FIGS. 14A–14C and FIG. 16, tip 313 further includes a proximal hub 506 for supporting a male electrical connector 508 that holds a plurality of wires 510 each coupled to one of the electrode terminals 358 and the return electrode 400 on support member 370. A female connector 520 housed within handle 312 is removably coupled to male connector 508, and a plurality of wires 522 extend from female connector 520 through a strain relief 524 to cable 334. Both sets of wires 510, 522 are insulated to prevent shorting in the event of fluid ingress into the probe 310. This design allows for removable connection of the electrodes in tip 313 with the connector 520 within handle 312 so that the handle can be re-used with different tips 313. Probe 310 will preferably also include an identification element, such as a coded resistor (not shown), for programming a particular voltage output range and mode of operation for the power supply. This allows the power supply to be employed with a variety of different probes for a variety of different applications.

Figure 13:
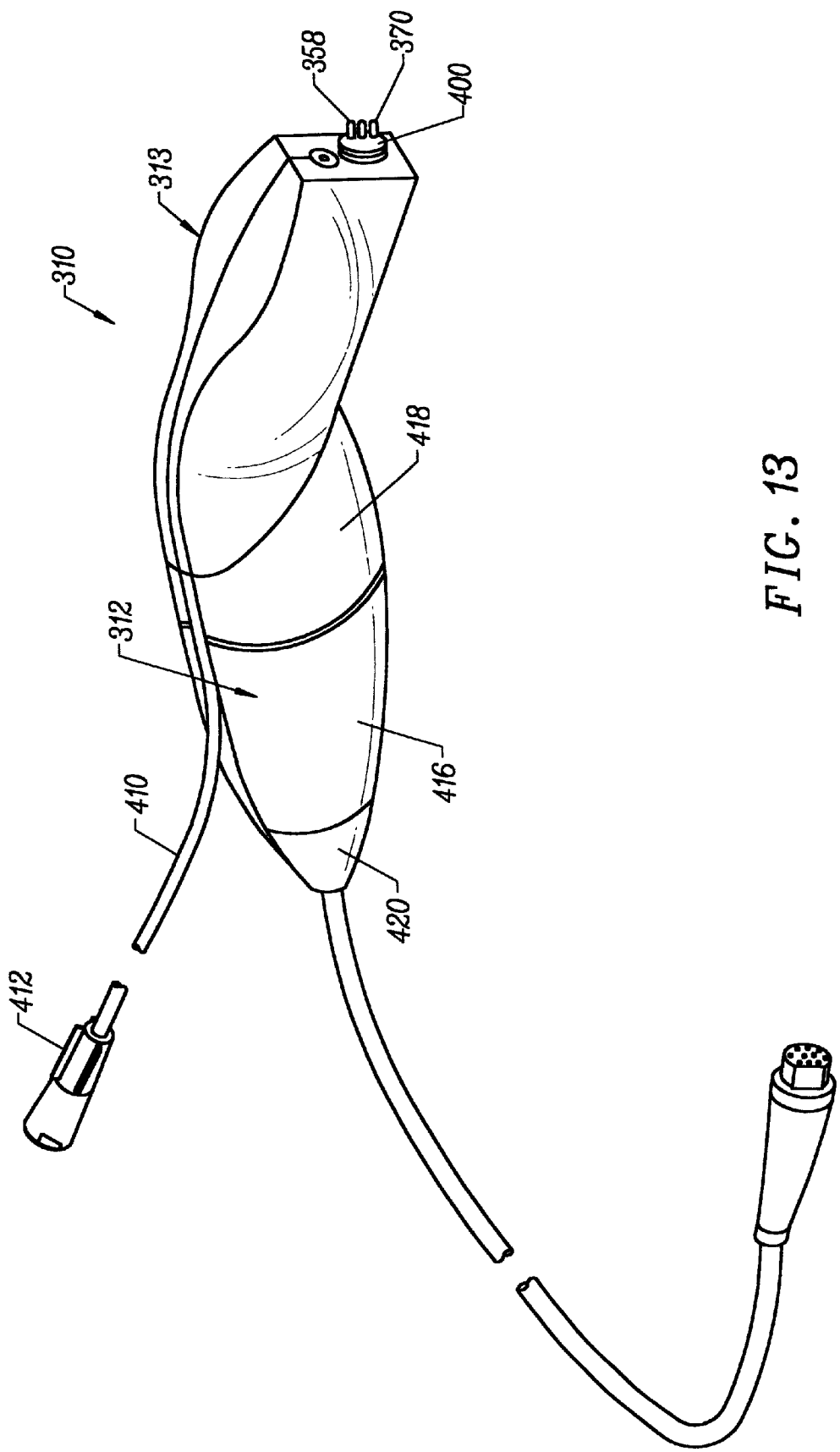
FIG. 13 is a perspective view of another embodiment of an electrosurgical probe for use in dermatology procedures.

In the representative embodiment, probe 310 includes a fluid tube 410 (FIG. 14) for delivering electrically conductive fluid to the target site. Fluid tube 410 is sized to extend through a groove 414 in handle 313 and through an inner cavity 412 in tip 312 to a distal opening 414 (FIG. 15) located adjacent electrode support member 370. Tube 410 extends all the way through inner cavity 412 to opening 414 to eliminate any possible fluid ingress into cavity 412. As shown in FIGS. 13 and 14, fluid tube 410 includes a proximal connector 412 for coupling to an electrically conductive fluid source 321.

Probe 310 will also include a valve or equivalent structure for controlling the flow rate of the electrically conducting fluid to the target site. In the representative embodiment shown in FIGS. 14A–14C, handle 312 comprises a main body 430 coupled between distal hub 418 and strain relief 420, and a rotatable sleeve 416 around main body 430. Distal hub 418 has an opening 419 for receiving proximal hub 506 of tip 313 for removably coupling the tip 313 to the handle 312. Sleeve 416 is rotatably coupled to strain relief 420 and distal hub 418 to provide a valve structure for fluid tube 410. As shown in FIG. 14A, fluid tube 410 extends through groove 414 from strain relief 420, through main body 430 and distal hub 420 to tip 313. Rotation of sleeve 416 will impede, and eventually obstruct, the flow of fluid through tube 410. Of course, this fluid control may be provided by a variety of other input and valve devices, such as switches, buttons, etc.

In alternative embodiments, the fluid path may be directly formed in probe 310 by, for example, a central inner lumen or an annular gap (not shown) within the handle and the tip. This inner lumen may be formed near the perimeter of the probe 310 such that the electrically conducting fluid tends to flow radially inward towards the target site, or it may be formed towards the center of probe 310 so that the fluid flows radially outward. In addition, the electrically conducting fluid may be delivered from a fluid delivery element (not shown) that is separate from probe 310. In arthroscopic surgery, for example, the body cavity will be flooded with isotonic saline and the probe 310 will be introduced into this flooded cavity. Electrically conducting fluid will be continually resupplied to maintain the conduction path between return electrode 400 and electrode terminals 358. A more complete description of alternative electrosurgical probes incorporating one or more fluid lumen(s) can be found in commonly assigned, co-pending application Ser. No. 08/485,219, filed on Jun. 7, 1995, the complete disclosure of which has previously been incorporated herein by reference.

Figure 16:
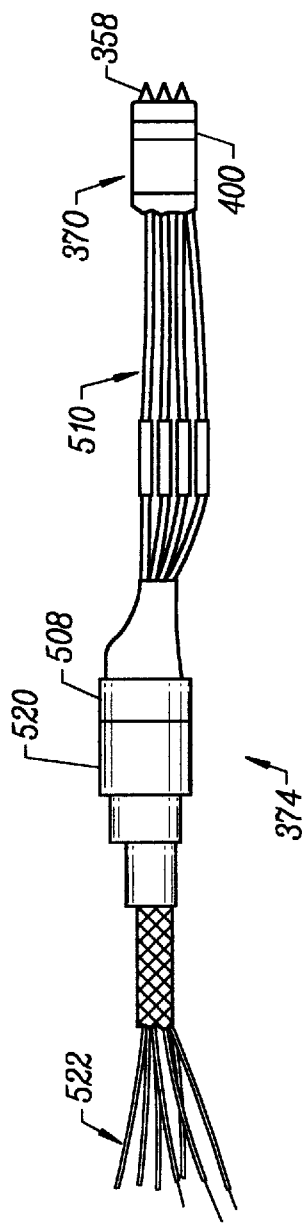
FIG. 16 illustrates the electrical connections and the electrode support of the handpiece in greater detail.
Figure 17:
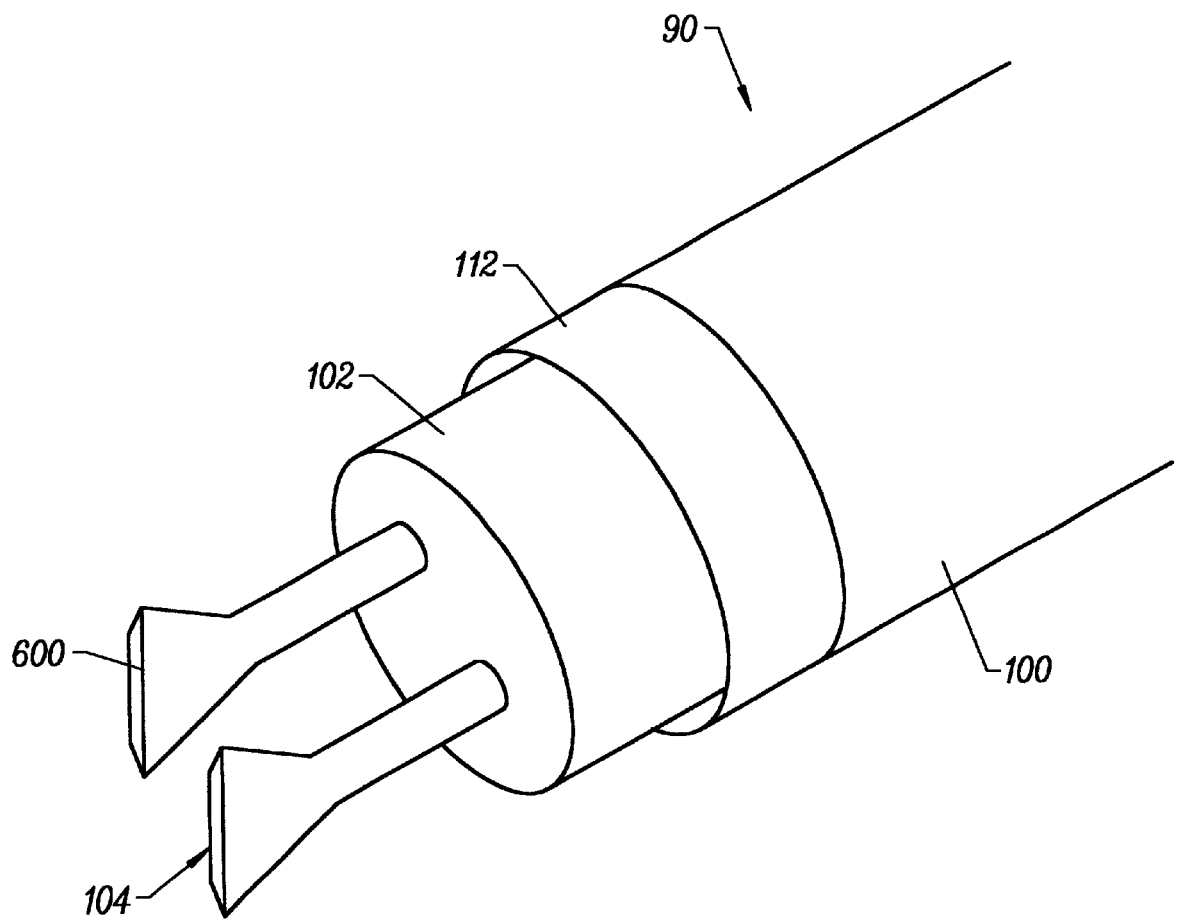
FIG. 17 is a perspective view of the distal portion of another electrosurgical probe according to the present invention.

Referring to FIGS. 15 and 16, electrically isolated electrode terminals 358 are spaced apart over tissue treatment surface 380 of electrode support member 370, preferably in a linear array. In the representative embodiment, three electrode terminals 358, each having a substantially conical shape, are arranged in a linear array extending distally from surface 380. Electrode terminals 358 will usually extend a distance of about 0.5 to 20 mm from tissue treatment surface 380, preferably about 1 to 5 mm. Applicant has found that this configuration increases the electric field intensities and associated current densities at the distal edges of electrode terminals 358, which increases the rate of tissue cutting. In the representative embodiment, the tissue treatment surface 380 has a circular cross-sectional shape with a diameter in the range of about 0.5 mm to 20 mm (preferably about 2 to 10 mm). The individual electrode terminals 358 preferably taper outward as shown, or they may form a distal edge, such as the electrodes shown in FIGS. 8A and 11.

Electrode support member 370 preferably comprises a multilayer substrate comprising a suitable high temperature, electrically insulating material, such as ceramic. The multilayer substrate is a thin or thick-film hybrid having conductive strips that are adhered to the ceramic wafer layers (e.g., thick-film printed and fired onto or plated onto the ceramic wafers). The conductive strips typically comprise tungsten, gold, nickel, silver, platinum or equivalent materials. In the exemplary embodiment, the conductive strips comprise tungsten, and they are co-fired together with the wafer layers to form an integral package. The conductive strips are coupled to external wire connectors by holes or vias that are drilled through the ceramic layers, and plated or otherwise covered with conductive material. A more complete description of such support members 370 can be found in U.S. patent application Ser. No. 08/977,845, filed Nov. 25, 1997, previously incorporated herein by reference.

Figure 18:
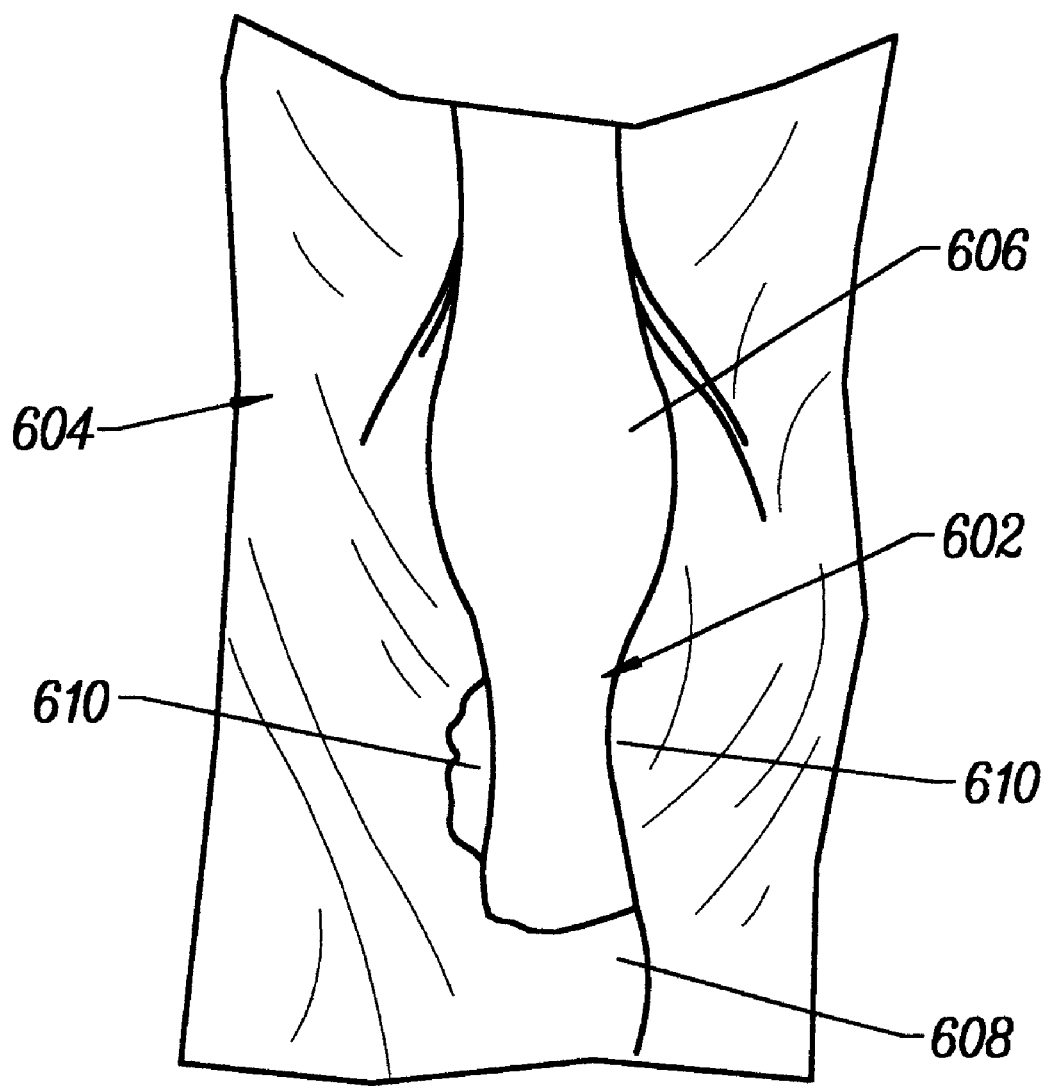
FIG. 18 illustrates a method of removing a patellar ligament with the probe of FIG. 17.

Referring now to FIGS. 17 and 18, a system and method for removing ligaments from a joint will now be described. As shown in FIG. 17, an electrosurgical probe 90 comprises a shaft 100 and at least two electrode terminals 104 extending from a support matrix 102 at the distal end of the shaft. The electrode terminals 104 preferably define a distal edge 600 for cutting an incision in tissue. The edges 600 of the electrode terminals 104 are substantially parallel with each other and usually spaced a distance of about 4 to 15 mm, preferably about 8–10 mm. The edges 600 extend from the distal end of support matrix 102 by a distance of about 0.5 to 10 mm, preferably about 2 to 5 mm. In the exemplary embodiment, probe 90 will include a return electrode 112 spaced proximally from the electrode terminals 104. Alternatively, the return electrode 112 may be one of the electrode terminals 104, or it may be a dispersive pad located on an external surface of the patient's body.

Referring now to FIG. 18, the probe 90 of FIG. 17 is particularly useful for removing a ligament from a joint, such as the patellar ligament 602 (or one of the cruciate ligaments) from the knee cavity 604. As shown, the patellar ligament 602 extends from the patella 606 down to the tibia 608. In ligament replacement procedures, the patellar ligament 602 is separated from the surrounding tissue 610 (typically with a scalpel) on either side of the ligament. The surgeon then severs the ligament 602 at the upper and lower portions thereof and removes the ligament from the patient's knee. One of the disadvantages with conventional scalpels is that they produce excessive bleeding, which obstructs visualization of the surgical site. In addition, the scalpels damage the surrounding tissue, which increases the patient's recovery time.

According to the present invention, the distal end portion of probe 90 (FIG. 17) is introduced into the knee cavity, and electrode terminals 104 are positioned on either side of patellar ligament 602 (FIG. 18). A high frequency voltage difference is applied between electrode terminals 104 and return electrode 112 and the probe 90 is translated along the length of the ligament 602 to separate the ligament from the surrounding tissue 610. The sharp edges of electrode terminals 104 facilitate cutting through tissue.

In an exemplary embodiment, the high frequency voltage is sufficient to convert the electrically conductive fluid (not shown) between the target tissue and electrode terminal(s) 104 into an ionized vapor layer or plasma (not shown). As a result of the applied voltage difference between electrode terminal(s) 104 and the target tissue (i.e., the voltage gradient across the plasma layer), charged particles in the plasma (viz., electrons) are accelerated towards the tissue. At sufficiently high voltage differences, these charged particles gain sufficient energy to cause dissociation of the molecular bonds within tissue structures. This molecular dissociation is accompanied by the volumetric removal (i.e., ablative sublimation) of tissue and the production of low molecular weight gases, such as oxygen, nitrogen, carbon dioxide, hydrogen and methane. The short range of the accelerated charged particles within the tissue confines the molecular dissociation process to the surface layer to minimize damage and necrosis to the underlying tissue and the adjacent ligament 602.

During the process, the gases may be aspirated through a suction tube (not shown) in the probe to a vacuum source. In addition, excess electrically conductive fluid, and other fluids (e.g., blood) will be aspirated from the target site to facilitate the surgeon's view. During ablation of the tissue, the residual heat generated by the current flux lines (typically less than 150° C.), will usually be sufficient to coagulate any severed blood vessels at the site. If not, the surgeon may switch the power supply 28 into the coagulation mode by lowering the voltage to a level below the threshold for fluid vaporization, as discussed above. This simultaneous hemostasis results in less bleeding and facilitates the surgeon's ability to perform the procedure.

What is claimed is:

1. A method for applying electrical energy to a target site on a body structure within or on a patient's body, the method comprising:

providing a return electrode and an electrode terminal electrically coupled to a high frequency voltage source;

directing an electrically conductive fluid to the target site along a fluid path;

positioning an electrosurgical probe adjacent to the body structure so that the electrode terminal is brought into at least partial contact or close proximity with the target site in the presence of the electrically conductive fluid;

positioning the return electrode at the target site so that the return electrode does not contact the body structure;

applying high frequency voltage between the electrode terminal and the return electrode such that an electrical current flows from the electrode terminal, through the region of the target site, and to the return electrode; and translating the electrode terminal relative to the body structure to cut through a portion of the body structure.

2. The method of claim 1 further comprising positioning the return electrode within the electrically conductive fluid to generate a current flow path between the return electrode and the electrode terminal.

3. The method of claim 1 further comprising positioning the return electrode at the target site proximal of the electrode terminal.

4. The method of claim 1 wherein the first positioning step comprises positioning the electrosurgical probe such that at least two electrode terminals are brought into at least partial contact with or close proximity to the target site in the presence of electrically conductive fluid.

5. The method of claim 4 wherein the electrode terminals each have an edge, the terminals being positioned such that the edges are linear, the method further comprising the step of translating the electrode terminals in the direction of the linear edges to product a cutting effect along the body structure.

6. The method of claim 1 wherein the electrosurgical probe comprises at least two pairs of electrode terminals extending from a distal end of the probe, each pair of electrode terminals forming a substantially linear electrode edge for cutting a substantially linear incision in the body structure, and the method further comprising the step of translating the at least two pairs of electrode terminals in the direction of the linear electrode edges to produce a cutting effect along the body structure.

7. The method of claim 1 wherein the target site is the knee, shoulder, hip, hand, foot, elbow, thoracic cavity, abdomen, spine, mouth, ear, nose or throat.

8. The method of claim 1 wherein the target site includes the epidermis or dermis of the patient's body.

9. The method of claim 1 wherein the electrosurgical probe has at least two spaced electrode terminals, the method further comprising:
 positioning the probe such that the electrode terminals are located on either side of a ligament;
 translating the probe along the ligament to remove or cut tissue along either side of the ligament; and
 removing the ligament from the patient's body.

10. The method of claim 9 wherein the ligament is the patellar ligament.

11. The method of claim 9 wherein the electrode terminals each have an edge, the method comprising positioning the probe such that the edges of the electrode terminals are substantially parallel with the ligament and translating the probe along the ligament to cut tissue on either side of the ligament.

12. A method for cutting tissue at a target site comprising:
 providing a return electrode and an electrode terminal electrically coupled to a high frequency voltage source;
 positioning an electrosurgical probe adjacent to the tissue so that the electrode terminal is brought into at least partial contact or close proximity with the tissue at the target site;
 positioning the return electrode at the target site so that the return electrode does not contact the tissue;
 applying high frequency voltage between the electrode terminal and the return electrode such that an electrical current flows from the electrode terminal, through the region of the target site, and to the return electrode;
 translating the electrode terminal along a cutting path such that the tissue is volumetrically removed along the cutting path.

13. The method of claim 12 further comprising:
 locating electrically conductive fluid between the electrode terminal and the tissue; and
 applying sufficient voltage to the electrode terminal in the presence of the electrically conductive fluid to vaporize at least a portion of the fluid between the electrode terminal and the tissue.

14. The method of claim 13 further comprising accelerating charged particles from the vaporized fluid to the tissue to cause dissociation of the molecular bonds within the tissue.

15. A method for applying electrical energy to a target site on a body structure within or on a patient's body, the method comprising:
 providing a return electrode and a plurality of electrode terminals electrically coupled to a high frequency voltage source, wherein the electrode terminals each have an edge, the terminals being positioned such that the edges are linear;
 positioning an electrosurgical probe adjacent to the body structure so that the electrode terminals are brought into at least partial contact or close proximity with the target site in the presence of electrically conductive fluid;
 applying high frequency voltage between the electrode terminals and the return electrode such that an electrical current flows from the electrode terminals, through the region of the target site, and to the return electrode; and
 translating the electrode terminals in the direction of the edges to produce a cutting effect along the body structure.

16. The method of claim 15 further comprising directing the electrically conductive fluid to the target site along a fluid path.

17. The method of claim 15 further comprising immersing the electrosurgical probe in a cavity at least partially filled with the electrically conductive fluid.

18. The method of claim 15 further comprising positioning the return electrode within the electrically conductive fluid to generate a current flow path between the return electrode and the electrode terminals.

19. The method of claim 15 further comprising positioning the return electrode at the target site proximal of the electrode terminals.

20. The method of claim 15 wherein the electrosurgical probe comprises at least two pairs of electrode terminals extending from a distal end of the electrosurgical probe, each pair of electrode terminals forming a substantially linear electrode edge for cutting a substantially linear incision in the body structure, and the method further comprising the step of translating the at least two pairs of electrode terminals in the direction of the linear electrode edges to produce a cutting effect along the body structure.

21. The method of claim 15 wherein the target site is the knee, shoulder, hip, hand, foot, elbow, thoracic cavity, abdomen, spine, mouth, ear, nose or throat.

22. The method of claim 15 wherein the target site includes the epidermis or dermis of the patient's body.

23. A method for applying electrical energy to a target site on a body structure within or on a patient's body, the method comprising:
 providing a return electrode and an electrosurgical probe having at least two spaced electrode terminals electrically coupled to a high frequency voltage source
 positioning the electrosurgical probe such that the electrode terminals are located on either side of a ligament in the presence of electrically conductive fluid;
 applying high frequency voltage between the electrode terminals and the return electrode such that an electrical current flows from the electrode terminals, through the region of the target site, and to the return electrode;
 translating the probe along the ligament to remove or cut tissue along either side of the ligament; and
 removing the ligament from the patient's body.

24. The method of claim 23 further comprising directing the electrically conductive fluid to the target site along a fluid path.

25. The method of claim 23 further comprising immersing the electrosurgical probe in a cavity at least partially filled with the electrically conductive fluid.

26. The method of claim 23 further comprising positioning the return electrode within the electrically conductive fluid to generate a current flow path between the return electrode and the electrode terminals.

27. The method of claim 23 wherein the ligament is the patellar ligament.

28. The method of claim 23 wherein the electrode terminals each have an edge, the method comprising positioning the probe such that the edges of the electrode terminals are substantially parallel with the ligament and translating the probe along the ligament to cut tissue on either side of the ligament.

29. A method for applying electrical energy to a target site on a body structure within or on a patient's body, the method comprising:
 providing a return electrode and an electrode terminal electrically coupled to a high frequency voltage source;
 positioning a distal portion of an electrosurgical probe adjacent to the body structure so that the electrode terminal is brought into at least partial contact or close proximity with the target site;
 immersing the distal portion of the electrosurgical probe in a cavity at least partially filled with the electrically conductive fluid;
 positioning the return electrode at the target site so that the return electrode does not contact the body structure;
 applying high frequency voltage between the electrode terminal and the return electrode such that an electrical current flows from the electrode terminal, through the region of the target site, and to the return electrode; and
 translating the electrode terminal relative to the body structure to cut through a portion of the body structure.

30. The method of claim 29 further comprising positioning the return electrode within the electrically conductive fluid to generate a current flow path between the return electrode and the electrode terminal.

31. The method of claim 29 further comprising positioning the return electrode at the target site proximal of the electrode terminal.

32. The method of claim 29 wherein the return electrode and the electrode terminal are spaced from each other on the distal portion of the electrosurgical probe.

33. The method of claim 29 wherein the first positioning step comprises positioning the electrosurgical probe such that at least two electrode terminals are brought into at least partial contact with or close proximity to the target site in the presence of electrically conductive fluid.

34. The method of claim 33 wherein the electrode terminals each have an edge, the terminals being positioned such that the edges are linear, the method further comprising the step of translating the electrode terminals in the direction of the linear edges to produce a cutting effect along the body structure.

35. The method of claim 29 wherein the electrosurgical probe comprises at least two pairs of electrode terminals extending from the distal portion of the electrosurgical probe, each pair of electrode terminals forming a substantially linear electrode edge for cutting a substantially linear incision in the body structure, and the method further comprising the step of translating the at least two pairs of electrode terminals in the direction of the linear electrode edges to produce a cutting effect along the body structure.

36. The method of claim 29 wherein the electrosurgical probe has at least two spaced electrode terminals, the method further comprising:
 positioning the probe such that the electrode terminals are located on either side of a ligament;
 translating the probe along the ligament to remove or cut tissue along either side of the ligament; and
 removing the ligament from the patient's body.

37. The method of claim 36 wherein the ligament is the patellar ligament.

38. The method of claim 36 wherein the electrode terminals each have an edge, the method comprising positioning the probe such that the edges of the electrode terminals are substantially parallel with the ligament and translating the probe along the ligament to cut tissue on either side of the ligament.

* * * * *